(12) United States Patent
Omasa

(10) Patent No.: US 6,605,252 B2
(45) Date of Patent: Aug. 12, 2003

(54) VIBRATIONALLY STIRRING APPARATUS FOR STERILIZATION, STERILIZING APPARATUS AND STERILIZING METHOD

(75) Inventor: Ryushin Omasa, Kanagawa (JP)

(73) Assignee: Japan Techno Co., Ltd., Tokyo (JP)

(*) Notice: Subject to any disclaimer, the term of this patent is extended or adjusted under 35 U.S.C. 154(b) by 179 days.

(21) Appl. No.: 09/761,051

(22) Filed: Jan. 16, 2001

(65) Prior Publication Data

US 2001/0053332 A1 Dec. 20, 2001

(30) Foreign Application Priority Data

May 2, 2000 (JP) .................................... 2000-133737
May 16, 2000 (JP) .................................... 2000-143890
Jul. 13, 2000 (JP) .................................... 2000-213538

(51) Int. Cl.$^7$ ............................................. A61L 2/00
(52) U.S. Cl. .................. 422/20; 205/742; 205/771; 366/118; 366/343; 422/28; 422/29; 422/292; 422/297; 422/300
(58) Field of Search ............................ 422/20, 28, 29, 422/292, 293, 297, 300; 205/742, 771, 548; 366/118, 343

(56) References Cited

U.S. PATENT DOCUMENTS

| | | |
|---|---|---|
| 5,375,926 A | 12/1994 | Omasa |
| 5,626,824 A | 5/1997 | Ishikawa et al. |
| 5,730,856 A | 3/1998 | Omasa |

FOREIGN PATENT DOCUMENTS

| | | |
|---|---|---|
| DE | 33 43 586 A1 | 6/1985 |
| DE | 36 28 012 A1 | 2/1988 |
| EP | 0 306 301 A | 3/1989 |
| EP | 1 050 336 A1 | 5/2000 |
| GB | 180 973 A | 11/1922 |

OTHER PUBLICATIONS

EP 01 10 1020, Aug. 10, 2001, European Search Report.
Patent Spedification [Second Edition], 180,973, Convention Date (Switzerland): Jun. 1, 1921—Application Date (in United Kingdom: Jul. 21, 1921. No. 19,673/21 Complete Accepted: Nov. 21, 1922. Complete Specification. A New or Improved Process of Sterilizing Liquids and Solid Materials or Appliances.

*Primary Examiner*—Krisanne Thornton
(74) *Attorney, Agent, or Firm*—Pitney, Hardin, Kipp & Szuch LLP

(57) ABSTRACT

A method of sterilizing liquid is performed by providing a vibrationally stirring apparatus having a vibration generating unit containing a vibration motor (14), a vibrating rod (7) operationally connected to the vibration generating unit, vibration vanes (10) fixed to the vibrating rod, and vibration vane fixing members (9) for fixing the vibration vanes to the vibrating rod, wherein the vibration vane (10) has a surface made of sterilizing metal and the vibration vane fixing member (9) is made of magnetic field generating material; submerging the vibration vanes and the vibration vane fixing members in the liquid (LIQ) taken in a treatment tank (13); and vibrating the vibration vane at an amplitude of 0.1 to 15.0 mm and at a vibrational frequency of 200 to 1000 times per minute by the vibration generating unit to cause vibrationally stirring of the liquid, thereby sterilizing the liquid.

42 Claims, 21 Drawing Sheets

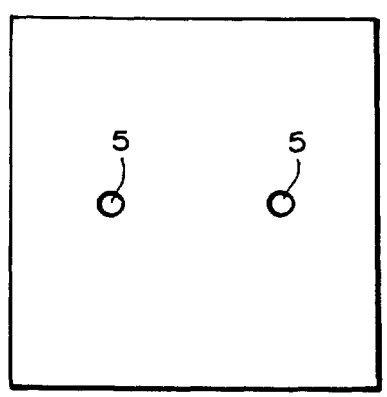
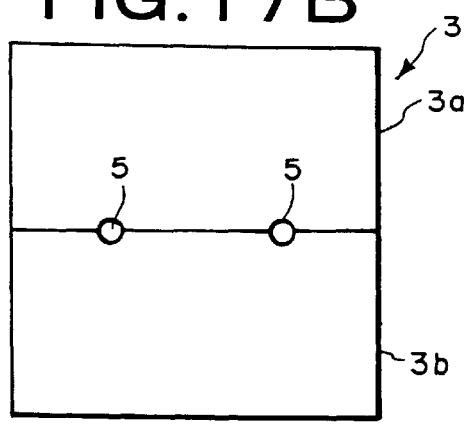
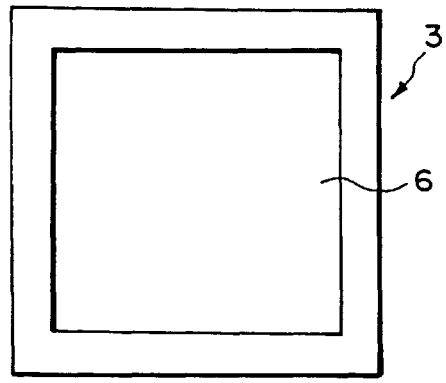
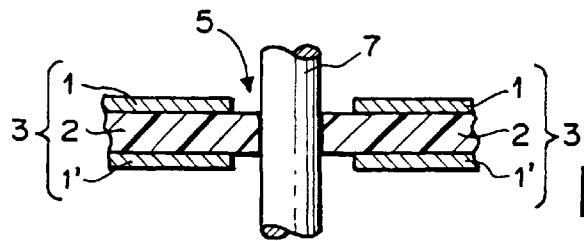
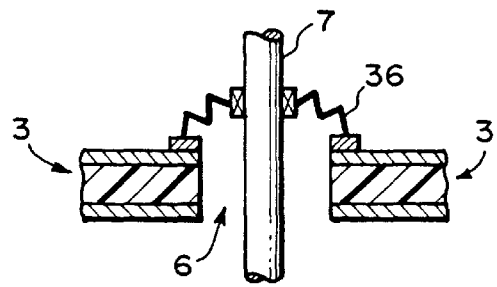

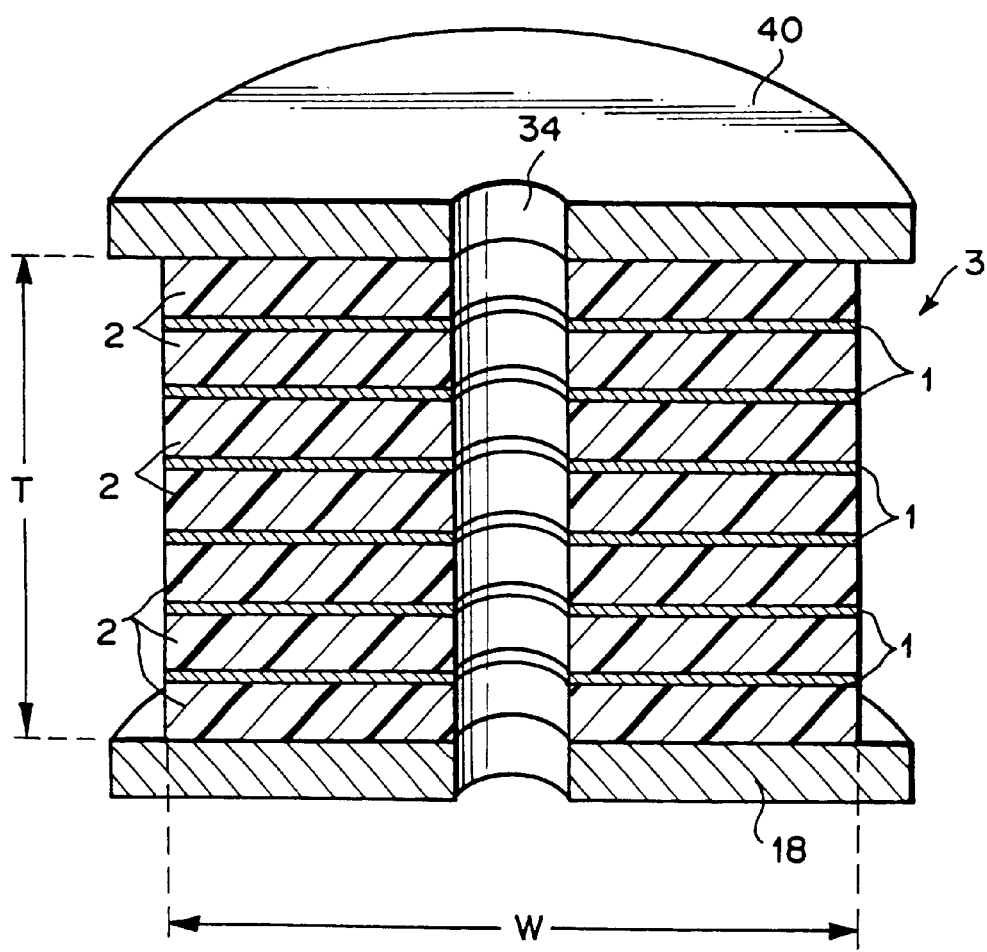

VIBRATIONALLY STIRRING APPARATUS FOR STERILIZATION, STERILIZING APPARATUS AND STERILIZING METHOD

BACKGROUND OF THE INVENTION

1. Field of the Invention

The present invention relates to a vibrationally stirring apparatus for sterilization, a sterilizing apparatus containing the vibrationally stirring apparatus and a sterilizing method for liquid or solid article by using the same.

2. Description of the Related Art

In a conventional sterilizing method for water, it has been adopted to pour oxidant such as sodium hypochlorite or the like into water to sterilize the water. However, this method causes water to smell of chlorine because chlorine ions remain in the treated water and thus water itself tastes bad. If the amount of chemicals is reduced to lower bad taste of the water, the sterilization effect is also lowered. On the other hand, if the amount of chemicals is increased, they are harmful to human beings. Therefore, this method should not be used if possible. Particularly in the case of drinking water stocked in tanks (water reservoirs) which are set up on the rooftops of buildings or the like, chemicals put in the water lose their effect, and thus the water in the tanks are actually contaminated and polluted with germs (bacteria) or micro dust in air. Therefore, it is indispensable to clean the inner surface of tanks and waste the remaining water in the tanks periodically.

On the other hand, a large amount of each kind of disinfectant is used for sterilization of medical instruments. Therefore, there are various problems containing not only a cost problem, but also a draining problem. Also there are various difficult problems to perform sterilization of tableware in hospitals, schools, etc.

SUMMARY OF THE INVENTION

Therefore, an object of the present invention is to provide a vibrationally stirring apparatus for sterilization, and a sterilizing apparatus which can supply sufficiently sterilized liquid or solid articles without using the disinfectant or sterilizing agent and a method of sterilizing liquid or solid articles by using the vibrationally stirring apparatus.

In order to attain the above object, according to a first aspect of the present invention, there is provided a vibrationally stirring apparatus for sterilizing liquid and/or an article submerged in liquid by vibrationally stirring the liquid, comprising:

a vibration generating unit containing a vibration motor;
at least one vibrating rod operationally connected to the vibration generating unit;
at least one vibration vane fixed to the vibrating rod; and
a vibration vane fixing member for fixing the vibration vane to the vibrating rod,
wherein the vibration vane and/or the vibration vane fixing member have a surface made of sterilizing metal and/or sterilizing metallic compound, and/or are made of magnetic field generating material.

In order to attain the above object, according to a second aspect of the present invention, there is provided a sterilizing apparatus for liquid and/or an article submerged in liquid, comprising:

the above vibrationally stirring apparatus; and
a treatment tank for receiving the liquid, in which the vibration vane and the vibration vane fixing member are disposed,
wherein the vibration vane and/or the vibration vane fixing member have a surface made of sterilizing metal and/or sterilizing metallic compound, and/or are made of magnetic field generating material.

A holder for holding the article in the treatment tank may be used. A driving means for moving the holder may be used.

In the present invention, for example, the sterilizing metal is silver, gold or alloy thereof, and the sterilizing metallic compound is titanium oxide or zinc oxide, and, the vibration generating unit vibrates the vibration vane at an amplitude of 0.1 to 15.0 mm and at a vibrational frequency of 200 to 1000 times per minute in the liquid, and an inverter for controlling the vibration motor may be used so as to vibrate at a frequency of 10 to 200 Hz.

The sterilizing apparatus of the present invention may have a device for irradiating the vibration vane and/or the vibration vane fixing member with ultraviolet-light, which is disposed at the inside or outside of the treatment tank.

In order to attain the above object, according to a third aspect of the present invention, there is provided a sterilizing method for liquid and/or an article submerged in liquid, comprising:

providing the above vibrationally stirring apparatus;
submerging the vibration vane and the vibration vane fixing member in the liquid taken in a treatment tank; and
vibrating the vibration vane at an amplitude of 0.1 to 15.0 mm and at a vibrational frequency of 200 to 1000 times per minute by the vibration generating unit to cause vibrationally stirring of the liquid, thereby sterilizing the liquid.

An article may be submerged in the liquid and sterilized by vibrationally stirring of the liquid. For example, the liquid is vibrationally stirred so as to have a flow rate of 100 mm/sec or more in each direction of three dimensions.

In the sterilizing method of the present invention, the liquid may be vibrationally stirred while irradiating the vibration vane and/or the vibration vane fixing member with ultraviolet-light.

The term "sterilization" or "sterilizing" in the present invention includes "pasteurization", "disinfection", "microbiostasis", "microbial control", "removal of microorganism" or "antimicrobial".

The present invention can be applied to the sterilization of liquid to be treated such as city water, water for preparing drinking water, water for swimming pool, water for bath, tea, juice, milk, or the like. In addition, the present invention can be applied to the sterilization of solid article to be treated such as fruits, vegetables, fishes, medical instruments and parts thereof, food manufacturing or processing instruments and parts thereof, clothings used in hospital, or the like. The solid article is subjected to washing treatment when the sterilization is performed.

Furthermore, the present invention can be applied to mixing liquid with the other material together with the sterilization and stirring thereof. Exemplary thereof is manufacturing various kinds of liquid edibles such as mixed juice, liquor, mayonnaise, processed milk, or the like, or thawing frozen foods such as frozen fishes in the liquid such as water.

According to the present invention, the following effects can be achieved.

(1) The present invention can provide new sterilizing and cleaning means using no chemicals. Further, the conventional sterilizing means needs a first washing treatment, subsequent chemical treatment and subsequent second washing treatment. Therefore, the number of steps is large. However, the present invention needs only one step.

(2) The present invention can provide water suitable for flower arranging.

(3) In the present invention, when magnetic materials are used, iron powders and iron colloid contained in water can be effectively removed.

(4) In the present invention, when magnetic materials are used, a large circulating amount of water passes through a strong magnetic field to make water clusters smaller and thus enhance the washing efficiency.

(5) Use of magnetic materials enables bacteria such as Colon bacillus, 0–157, Salmonella, Streptococcus, etc. to be extremely effectively captured.

(6) The present invention is extremely effective to sterilize water tanks installed on the rooftops of buildings and water stocked in the water tanks. Further, it is also extremely effective to sterilize water pools and water therein.

(7) The present invention is extremely effective to sterilize tableware in hospitals, restaurants, schools, etc. and other associated instruments, and thus it greatly contributes to prevention of food poisoning. Further, if the present invention is applied to vegetables/fruits, the washing and the sterilization can be performed by only one step. Further, drinks themselves can be effectively sterilized.

(8) The present invention is effective to wash and sterilize medical instruments, bedclothes and hospital equipment, and also extremely effective to prevent in-hospital infection.

(9) The present invention can be practically used or performed under room temperature, and thus a treatment target is not deteriorated by heat. Further, the present invention uses the sterilizing means which uses substantially no chemical, and thus it is remarkably friendly to the earth environment.

(10) The present invention can provide sterilizing means which is effective to supply drinking water.

BRIEF DESCRIPTION OF THE DRAWINGS

FIG. 17A is a plan view of a vibration absorbing member;

FIGS. 17B and 17C are a plan view of variation of the vibration absorbing member;

FIGS. 17D and 17E are a cross-sectional view of the vibration absorbing member;

FIG. 19 is a partially cross-sectional, perspective view of a variation of the vibration absorbing member;

DETAILED DESCRIPTION OF THE PREFERRED EMBODIMENTS

Preferred embodiments according to the present invention will be described hereunder with reference to the accompanying drawings.

An embodiment of a sterilizing apparatus according to the present invention will be described in detail with reference to FIGS. 1 and 2.

Figure 1:
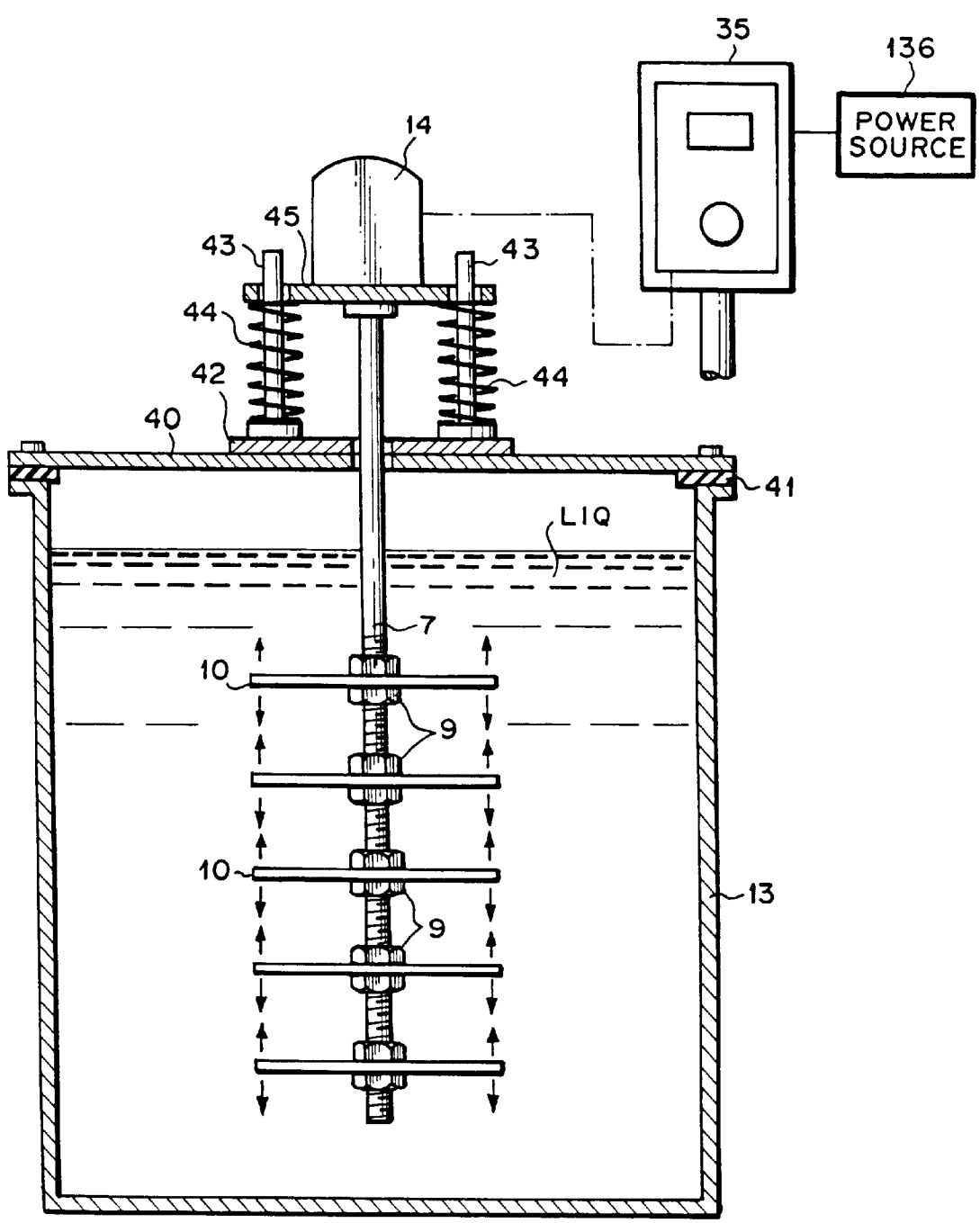
FIG. 1 is a cross-sectional view showing an embodiment of a sterilizing apparatus containing a vibrationally stirring apparatus according to the present invention.
Figure 2:
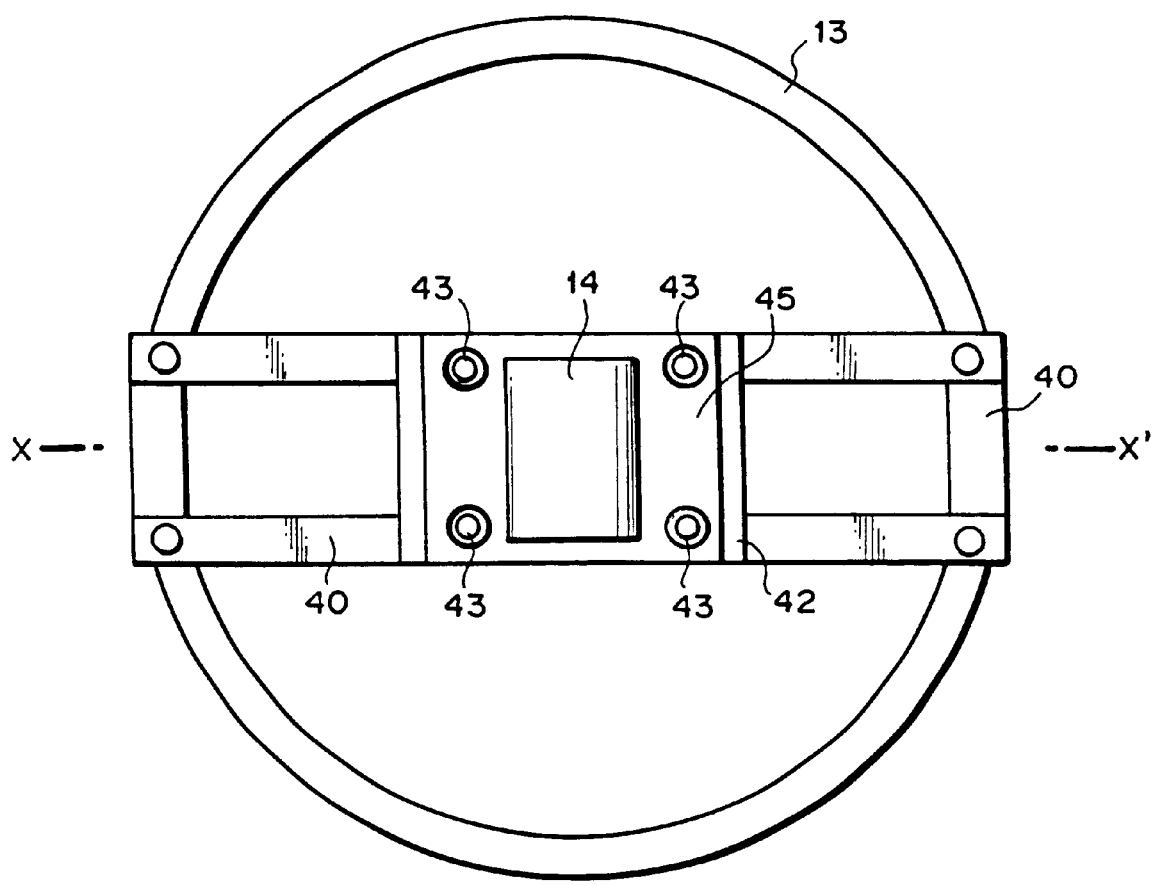
FIG. 2 is a plan view of the apparatus of FIG. 1.

FIG. 1 shows an embodiment of a sterilizing apparatus of the present invention, and it is a longitudinally cross-sectional view of the apparatus. FIG. 2 is a plan view of the apparatus. The sterilizing apparatus has a top-open type circular treatment tank (sterilizing chamber) 13, in which treatment liquid LIQ, e.g. water to be treated, is charged. A mount table 40 is fixed to the peripheral top edge of the treatment tank 13 via a vibration absorbing member 41. A vibrationally stirring apparatus according to the present invention is mounted on the mount table 40.

The vibrationally stirring apparatus has a base member 42 fixed to the mount table 40, four vertical guide shafts 43 lower ends of which are fixed to the mount table 40, four coiled springs 44 disposed around the guide shafts 43, and a motor mount plate 45 placed on the upper ends of the coiled springs 44. The upper portion of the guide shafts 43 pass through openings formed in the motor mount plate 45, and restrict the horizontal movement of the mount plate 45 within certain range. The coiled springs 44 act as vibration absorbing means. In place of the springs 44, a cushion member such as rubber plate or the like may be used. In this case, the guide shafts 43 and the cushion member are located at different positions. The springs 44 constitute a vibration absorption mechanism to prevent the vibration from motor mount plate 45 to the tank 13.

The vibrationally stirring apparatus has a vibration motor 14 secured to the mount plate 45. These constitutes a vibration generating unit. The mount plate 45 is movable in vertical direction along the guide shafts 43. A vibrating rod 7 is connected to the mount plate 45 at the upper end of the rod. The vibrating rod 7 extends vertically through openings formed in the base member 42 and mount table 40 into the treatment tank 13. Five vibration vanes 10 each having a surface made of at least one kind sterilizing or bactericidal metal are non-rotatably fixed to the vibrating rod 7 by vibration vane fixing members (preferably formed of magnetic material) which are nuts 9 engaged with a male screw formed on the vibrating rod 7 and fixing plates (not shown) each being interposed between the nut 9 and the vibration vane 10. Each vibration vane 10 is secured by a pair of the upper side and lower side nuts 9.

A transistor inverter 35 for controlling the number of vibration (frequency) of the vibration motor 14 is interposed in the power supplying line between a power source 136 and the vibration motor 14. The springs 44 absorb a part of vibration energy generated by the vibration motor 14 so that the transmission of vibration energy to the treatment tank 13 is inhibited. The remaining part of the vibration energy is transmitted to the vibrating rod 7, then to the vibration vanes 10. The vibration energy is transmitted from the vibration vanes 10 to water to be treated, and the water is vibrated and made flow.

The vibration motor 14 is operated to vibrate at any specific frequency in the range from 10 Hz to 200 Hz, preferably from 20 Hz to 60 Hz under control with the inverter 35, and the material and thickness of the vibration vanes are preferably set so that the vibration vanes are vibrated in the treatment liquid LIQ with flexibility on the basis of the vibration energy transmitted from the vibrating rod 7.

Each vane is formed of metal plated with sterilizable metal or plastics plated with sterilizable metal so as to have a thickness of 1.5 mm, for example. Each vane is set to be horizontal.

Further, each vibration vane is preferably designed in shape so as to have no notch. If each vibration vane has a notch, there would occur such a disadvantage that the vane is cracked from the notch portion due to material fatigue caused by the vibration. Each vibration vane is most preferably designed in such a stripe shape that the bulk portion other than the tip portion of the vibration vane has the same width as the base portion thereof which is fixed to the vibrating rod 7.

Figure 3:
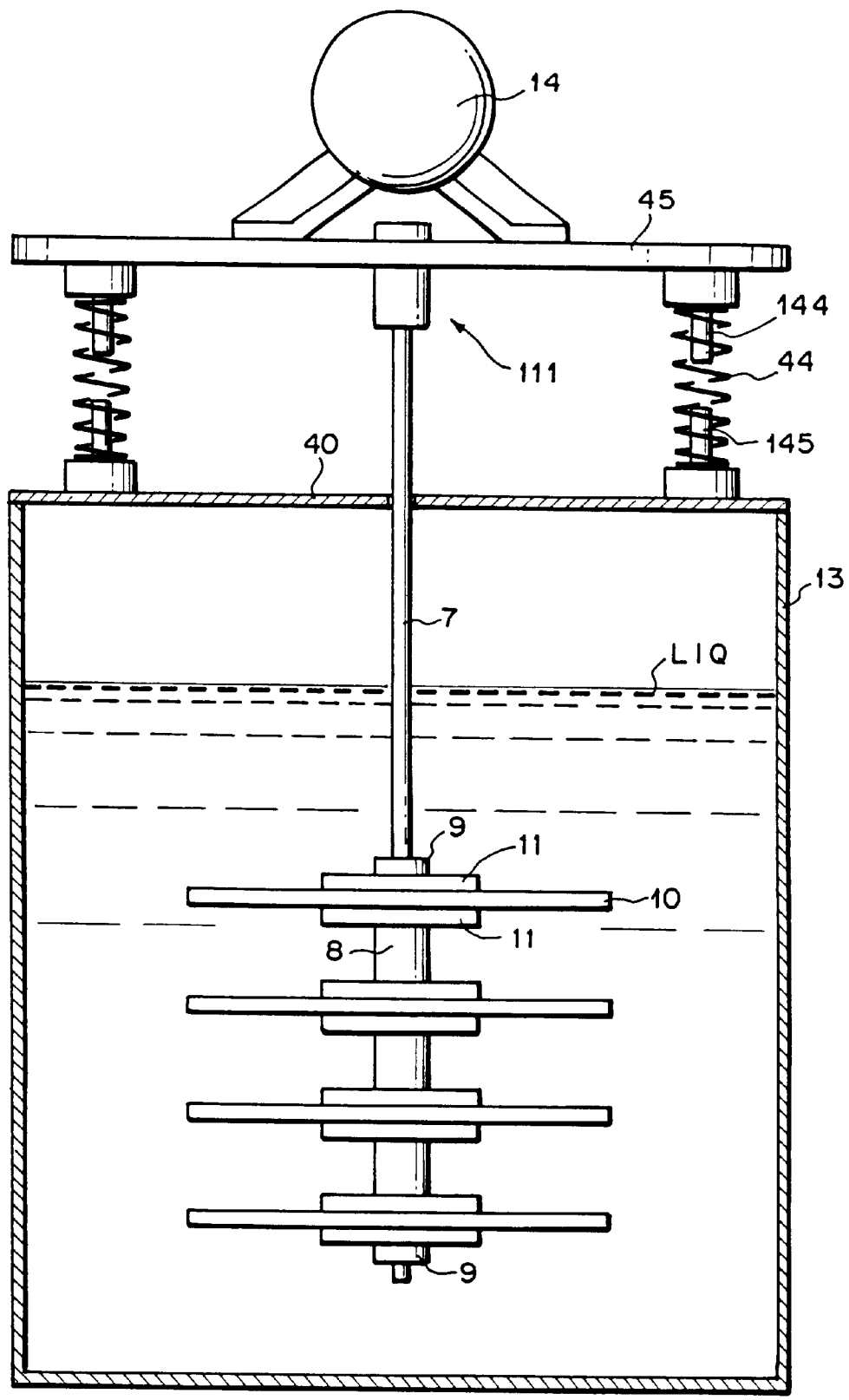
FIG. 3 is a cross-sectional view showing another embodiment of the apparatus according to the present invention.

In the present invention, it is preferable to provide a vibration stress dispersing unit. FIG. 3 shows an embodiment of a water sterilizing apparatus using the vibration stress dispersing unit. In this embodiment, upper guide rods 144 are secured to the mount plate 45, and lower guide rods 145 are secured to the mount table 40. The corresponding upper and lower guide rods 144, 145 are disposed in alignment with each other in vertical direction so as to form a gap therebetween. A spacer 8 is disposed between the adjacent vibration vanes 10. Vibration vane fixing members 11 are disposed at the upper and lower sides of each vibration vane 10. In the present invention, "vibration vane fixing member" means not only the fixing member 11 but also its accessories such as the spacer 8, nut 9 or the like.

For example, the following means may be used as the vibration stress dispersing unit constituting a connection portion 111 of the mount plate 45 with the vibrating rod 7. For example, a rubber ring may be provided as the vibration stress dispersing unit around the vibrating rod 7 at the lower and/or upper sides of the mount plate 45 in the connection portion 111. The rubber ring is preferably designed to have a large thickness.

Figure 4:
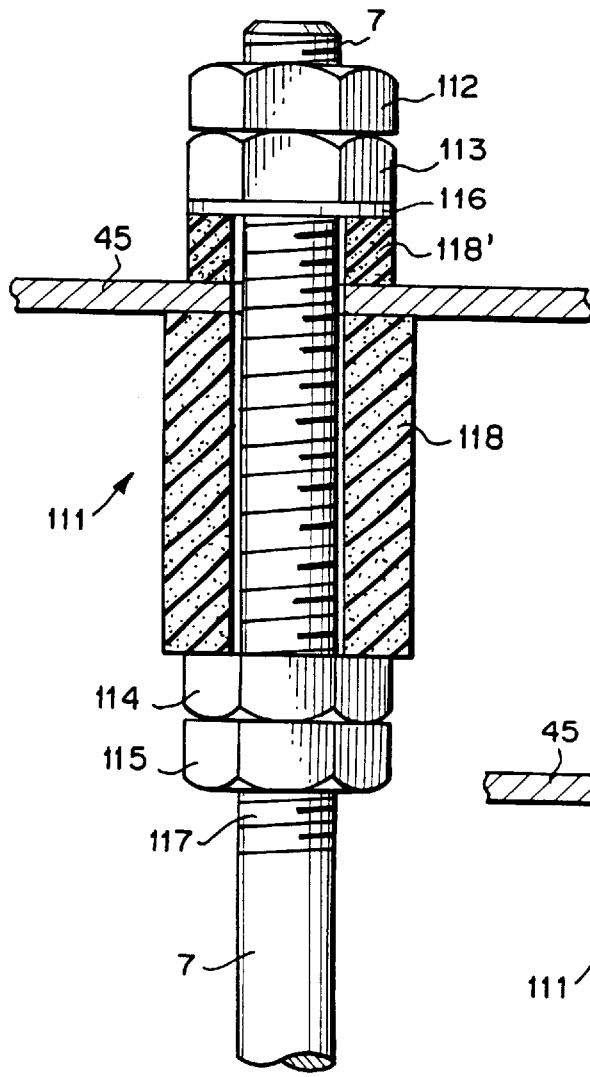
FIG. 4 shows an enlarged cross-section of a vibration stress dispersing unit.
Figure 5:
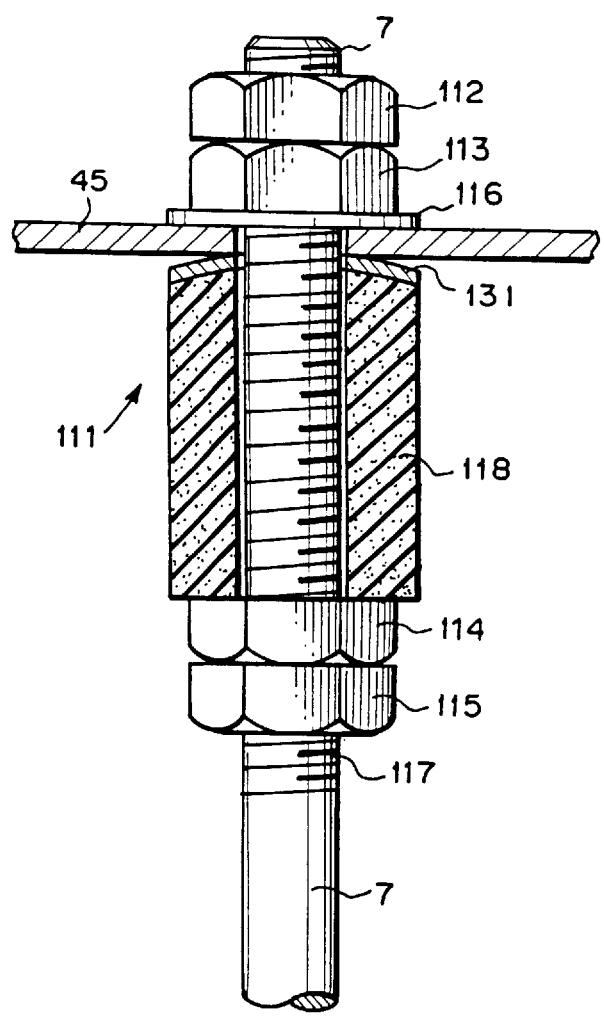
FIG. 5 shows an enlarged cross-section of another vibration stress dispersing unit.

Examples of the vibration stress dispersing unit are shown in FIGS. 4 and 5. The vibrating rod 7 is connected to the mount plate 45 which functions as a vibration transfer member from the vibration motor 14 to the vibrating rod 7. The vibrating rod 7 extends through a predetermined opening of the mount plate 45, and the upper end portion of the vibrating rod 7 is fixed by nuts 112, 113, 114, 115 and a washer ring 116. The nuts 112, 113, 114, 115 are engaged with a male screw 117 formed on the vibrating rod 7. In the case of FIG. 4, a rubber ring 118 is interposed between the mount plate 45 and the nut 114, and a rubber ring 118' is interposed between the mount plate 45 and the washer ring 116. In the case of FIG. 5, a rubber ring 118 and a washer ring 131 is interposed between the mount plate 45 and the nut 114. The nuts 112, 113, 114, 115 are engaged with the male screw 117 formed on the vibrating rod 7.

In the case where neither the rubber ring 118 nor the rubber ring 118' are used, the vibration stress is concentrated on the connection portion 111 and the surrounding portion thereof, and thus the vibrating rod 7 is liable to be broken. However, by inserting and fitting the rubber ring(s), this problem can be perfectly solved. Particularly when no rubber ring is used and the number of vibration of the vibration motor 14 is set to 100 Hz or more, the vibrating rod 7 is often broken. However, use of the rubber ring(s) enables the number of vibration to be increased with paying no attention to the above problem.

The rubber ring may be formed of hard elastic material such as hard natural rubber, hard synthetic rubber, synthetic resin or the like which has Shore "A" hardness of 80 to 120, preferably 90 to 100. Particularly, hard urethane rubber having Shore "A" hardness of 90 to 100 is preferable from the viewpoint of durability and resistance to chemicals.

In the connection portion 111, a stopper ring may be used instead of the nut. The stopper ring grasps the vibrating rod 7, so that the vibration vanes 10 can be positioned at the levels suitable for the inner size of the treatment tank 13 used.

A vibrating vane portion comprises vibration vanes 10 and vibration vane fixing members 11 including its accessories. The vibration vane may be constructed by a plurality of stacked vane plates, and the vibration vane and the vibration vane fixing member may be integrally formed with each other.

Each vibration vane is preferably formed of thin metal, elastic synthetic resin or the like, and the thickness thereof is set to such a value that the tip portion of each vibration vane exhibits a fluttering phenomenon (i.e. the tip portion of the vane is kept wavy) due to the vertical vibration of the vibration motor 14, thereby applying not only vibration but also fluidity to the liquid to be treated. For example, titanium, aluminum, copper, stainless steel, magnetic metal such as magnetic steel, or alloy thereof may be used as the material of the metal vibration vane. Further, polycarbonate, vinyl chloride resin, polypropylene, or the like may be used as the material of the synthetic resin vibration vane.

The thickness of the vibration vane to transmit the vibration energy and enhance the effect of the vibrational stirring is not limited to a specific value. However, in the case of the metal vibration vane, the thickness is preferably set to 0.2 mm to 2 mm, and in the case of the plastic vibration vane, the thickness is preferably set to 0.5 mm to 10 mm. If the thickness is excessively large, the vibrational stirring effect is reduced.

When the elastic synthetic resin or the like is used as the material of the vibration vane, the thickness is not particularly limited to a specific value, however, it is preferably set to 0.5 mm to 5 mm. When the vibration vane is formed of metal, for example, stainless steel, the thickness is set to 0.2 mm to 1 mm, more preferably 0.6 mm. Further, the amplitude of the vibration vane is preferably equal to 0.1 mm to 15 mm, more preferably to 0.5 mm to 5 mm.

The vibration vane may be secured to the vibrating rod at one stage or plural stages. When the vibration vane is secured over plural stages, the number of stages is varied in accordance with the level of treatment liquid such as water, the volume of the treatment tank and the size of the vibration motor, and it is set to 5 to 7 as occasion demands. In the case where the number of stages is increased, the amplitude of the vibration is reduced as the load of the vibration motor is increased, and the vibration motor may be heated. The vibration vanes may be integrally formed with one another.

Figure 6:
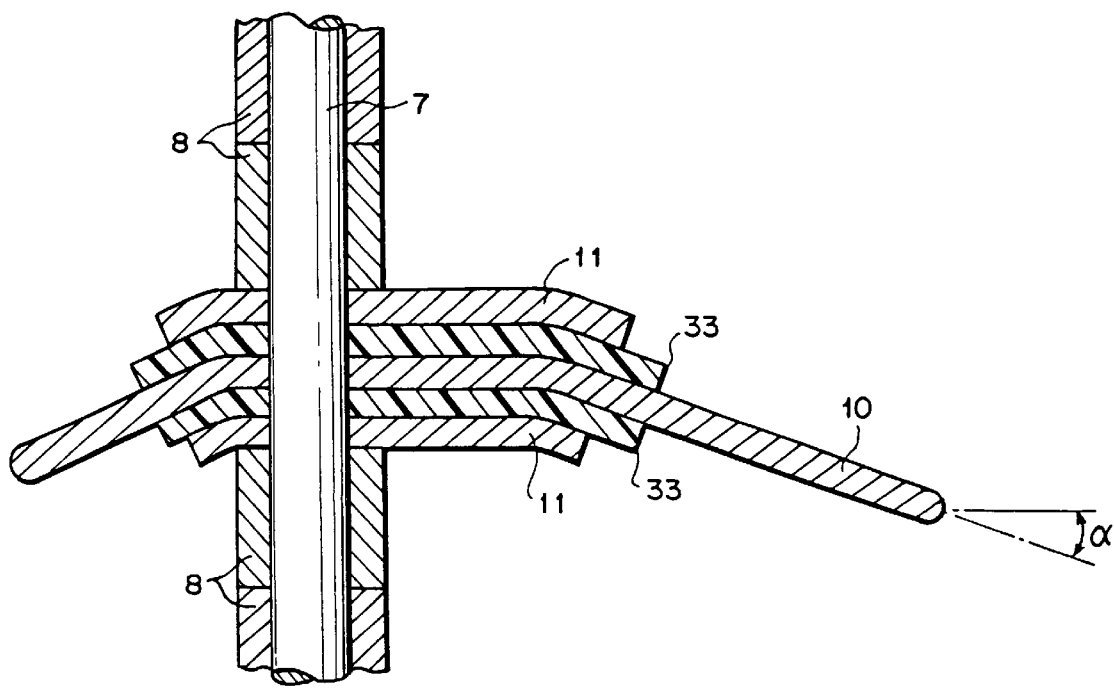
FIG. 6 is a cross-sectional view showing a vibrating vane portion.

The vibration vane may be set horizontally, however, it may be set to make some angle relative to the horizontal plane as shown in FIG. 6. The angle $\alpha$ is set to 5 to 30 degrees, particularly 10 to 20 degrees to make the vibrational stirring have directivity.

Each vibration vane is clamped from both the upper and lower sides thereof by the vibration vane fixing members to fix the vibration vane to the vibrating rod, thereby forming the vibrating vane portion. The vibration vane fixing members and the vibration vanes are integrally inclined as shown in FIG. 6.

The vibration vanes and the vibration vane fixing members may be manufactured by an integral molding method using plastic material. In the case where the vibration vane and the vibration vane fixing member are separately manufactured, the substance in the liquid to be treated is impregnated into the connection portion therebetween and fixed there, and thus much labor is needed to carry out a cleaning work. However, the integral molding method can avoid the above disadvantage. Further, by integrating the vane and the fixing member, no discontinuity in thickness occurs, and the concentration of stress can be avoided, so that the lifetime of the vanes can be greatly increased.

On the other hand, if the vibration vane and the vibration vane fixing member are separately manufactured, only the vibration vane can be substituted by another vibration vane. However, the exchange is also possible in the case of the integrally-molded article. In this case, the material of the vibration vane, the vibration vane fixing member and the integrally-molded article are not limited to plastic materials, and various materials as described above may be used. The vibration vane fixing members 11 clamping the vibration vane 10 from the upper and lower sides may be designed so that the upper and lower fixing members are different in size, whereby the vibration stress can be dispersed.

As shown in FIG. 6, a synthetic resin sheet such as a fluorine plastic sheet or a rubber sheet 33 is interposed between the vibration vane fixing member 11 and the vibration vane 10 to take a cushion action, thereby dispersing the stress in the vibration vane. Further, the synthetic resin sheet or the rubber sheet 33 is preferably designed to be longer than the vibration vane fixing member 11 and slightly project toward the tip end of the vibration vane 10 as shown in FIG. 6.

The vibrating vane portion comprising the vibration vane and the vibration vane fixing member can be firmly fixed to the vibrating rod by using a nut. When a plurality of vibration vanes are secured to the vibrating rod, they are fixed to the vibrating rod with nuts 9 and then one (FIG. 3) or plural (FIG. 6) cylindrical spacer 8 having a fixed length are inserted so as to be just fitted to the vibrating rod, whereby the interval between the adjacent vibration vanes can be easily fixed.

Various shapes may be adopted for the vibration vanes (or vibrating vane portion). FIGS. 7A and 7B and FIGS. 8A and 8B show examples of the shape of the vibration vanes.

Figure 7A:
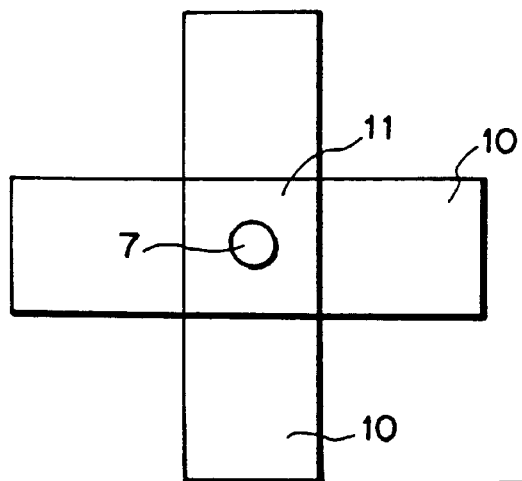
FIGS. 7A and 7B are each a plan view of a vibration vane.
Figure 7B:
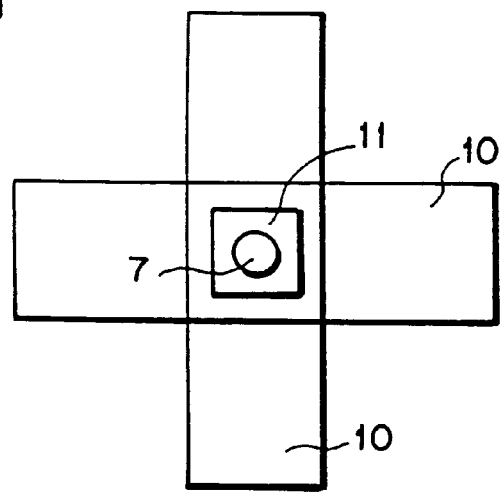
Figure 8A:
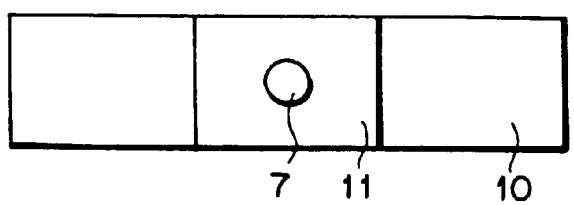
FIGS. 8A and 8B are each a plan view of a vibration vane.
Figure 8B:
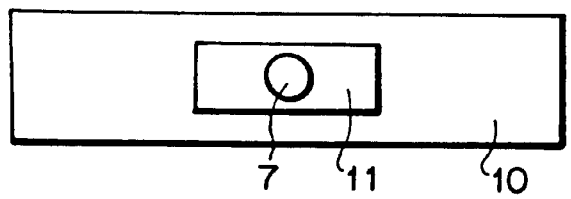

The vibration vane 10 shown in FIG. 7A may be formed by cutting out a cross-shaped portion from a plate or by superposing two stripes. The fixing member 11 may have the same width as the vibration vanes (FIG. 7A, FIG. 8A), or may be less than the width of the vibration vanes (FIG. 7B, FIG. 8B). In these cases, when a notch is formed in the vibration vane, the vibration vane and the fixing member trend to be damaged if it is used for a long time. Therefore, it is preferable to form no notch.

Figure 9:
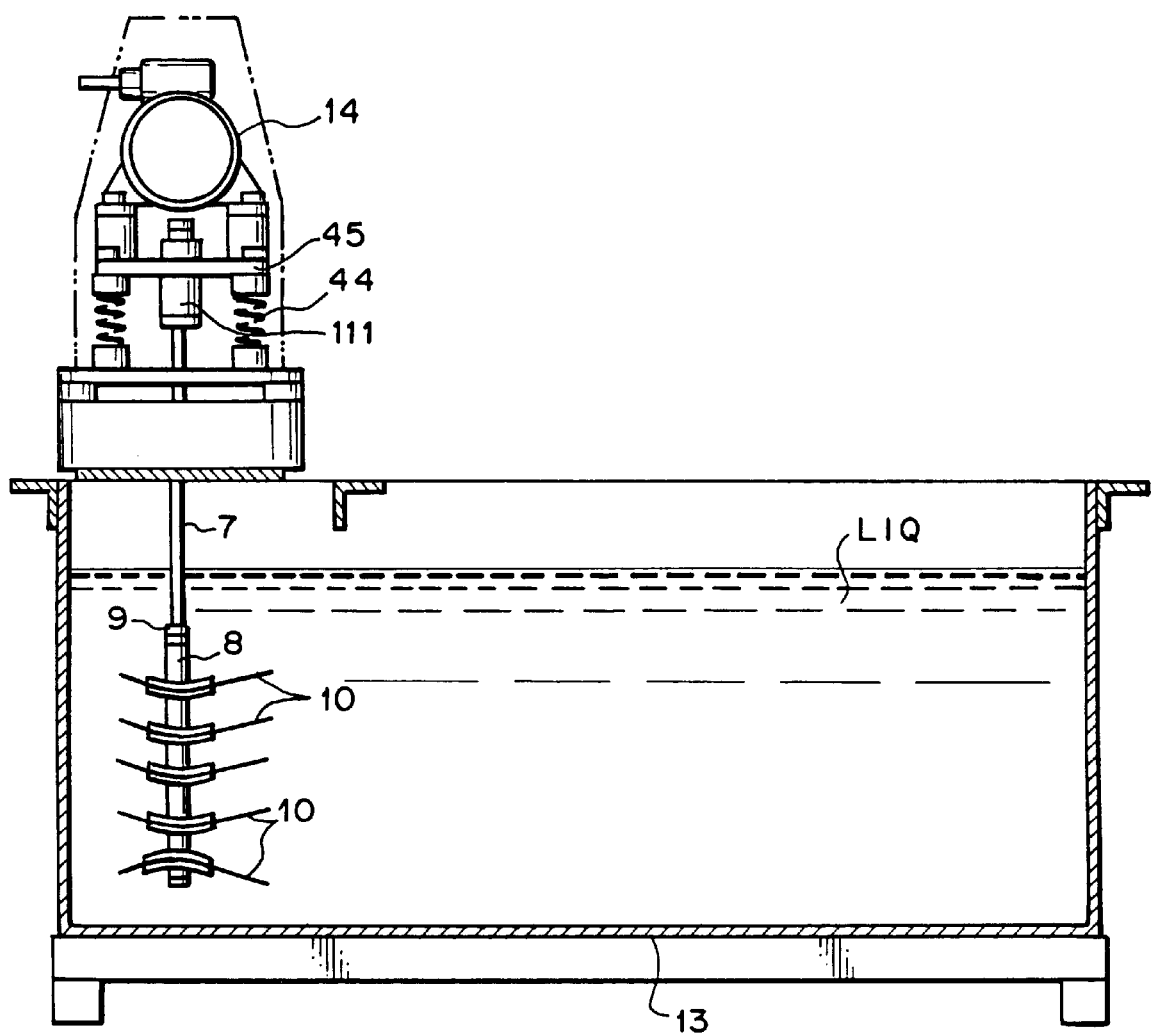
FIG. 9 is a cross-sectional view showing still another embodiment of the apparatus according to the present invention.
Figure 10:
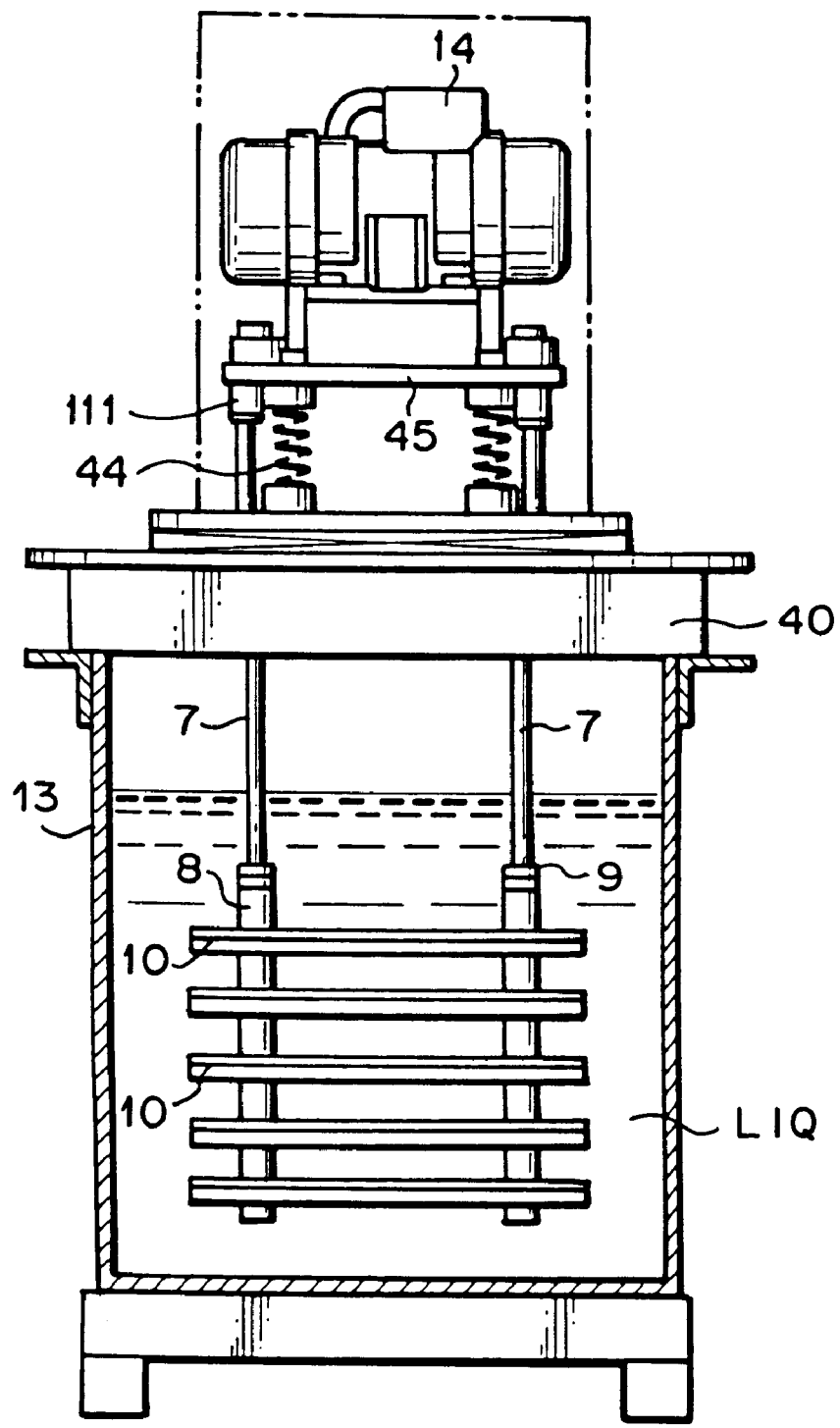
FIG. 10 is another cross-sectional view of the apparatus of FIG. 9.
Figure 11:
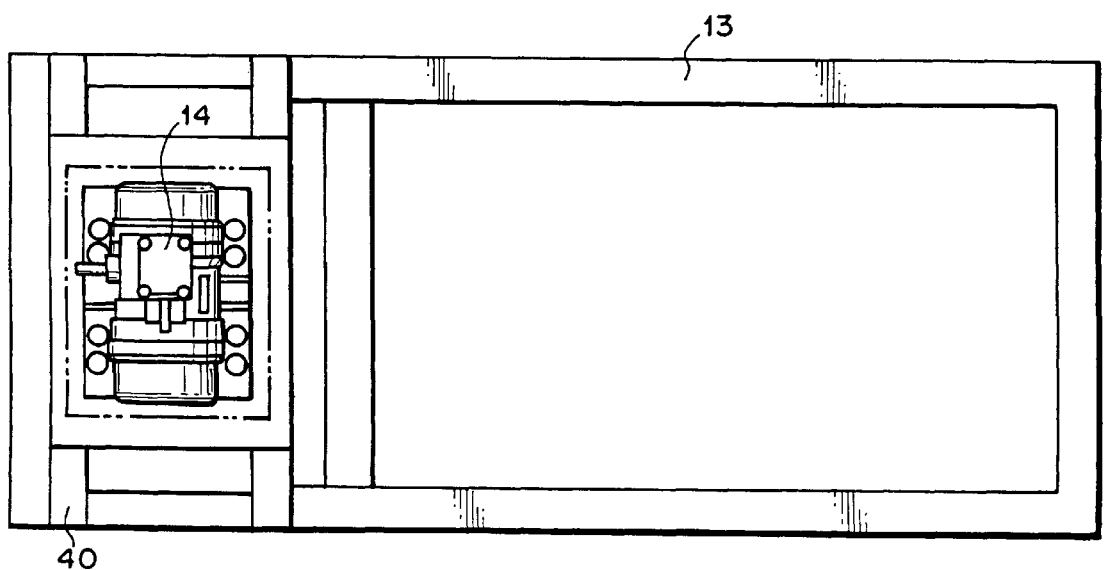
FIG. 11 is a plan view of the apparatus of FIG. 9.

In the above embodiments, one vibration rod 7 is provided. However, a plurality of vibration rods may be provided to achieve a multi-rod type sterilizing apparatus. The multi-rod design is effective to stir the liquid to be treated in a large-scale treatment tank. This embodiment is shown in FIGS. 9 to 11. In this embodiment, two vibration rods 7 are provided.

When the angle $\alpha$ is given to the vibration vane as shown in FIG. 6, one or two lower vibration vane of plural vibration vanes may be downwardly inclined, and the other vibration vanes may be upwardly inclined, as shown in FIG. 9. With this design, the bottom portion of the treatment tank 13 can be sufficiently stirred, and the liquid LIQ to be treated can be prevented from being stagnant at the lower portion in the tank.

The vibration motor 14 is set on the treatment tank 13 in the above embodiment. Alternatively, the vibration motor may be set on the side wall of the tank, and when the thickness of the tank is small (e.g. 5 mm or less in case of stainless steel tank) and thus the side wall of the tank is easily vibrated by the vibration energy of the liquid, it is preferable to mount the vibration motor on a table on the floor outside of the tank. Furthermore, if the thickness of the tank is equal to 5 mm or less, an enforcing member is affixed to the side wall of the tank as if a band is fastened, and the vibrationally stirring apparatus is mounted on the enforcing member.

Figure 12:
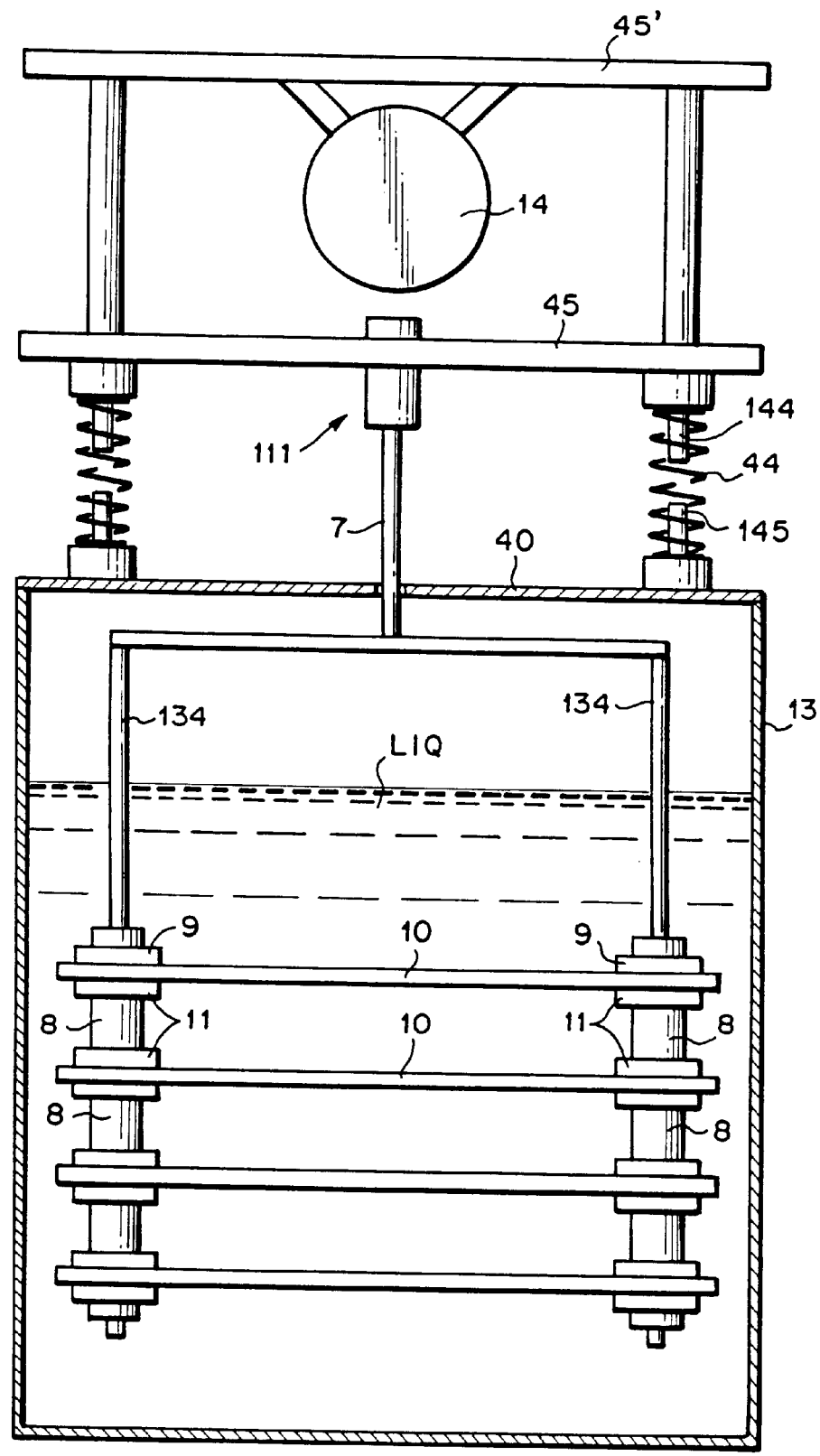
FIG. 12 is a cross-sectional view showing still another embodiment of the apparatus according to the present invention.

The vibration generating unit of the present invention adopts a system of vibrating the motor mount plate and transmitting the vibration energy of the mount plate to the vibrating rod. FIG. 12 shows a variation of the vibration generating unit, in which the vibration motor 14 is secured to the lower surface of the supplemental mount plate 45'. The supplemental mount plate 45' is mounted on the mount plate 45. With this structure, the center of gravity can be lowered to prevent occurrence of rolling at maximum as compared with the case where the vibration motor 14 is secured to the upper surface of the supplemental mount plate 45'.

In the embodiment of FIG. 12, the vibration rod 7 is divided into two divisional vibration rods 134 at some midpoint thereof, and the vibration vanes 10 are bridged between these divisional vibration rods 134 so that vibration of the vibration vanes applies vibrational stirring to the liquid LIQ to be treated.

In the present invention, the vibration motor may be a mechanical motor, a magnet motor, an air motor or the like. In place of the vibration motor, an air gun or the like may be used as the vibration generating unit.

Figure 13:
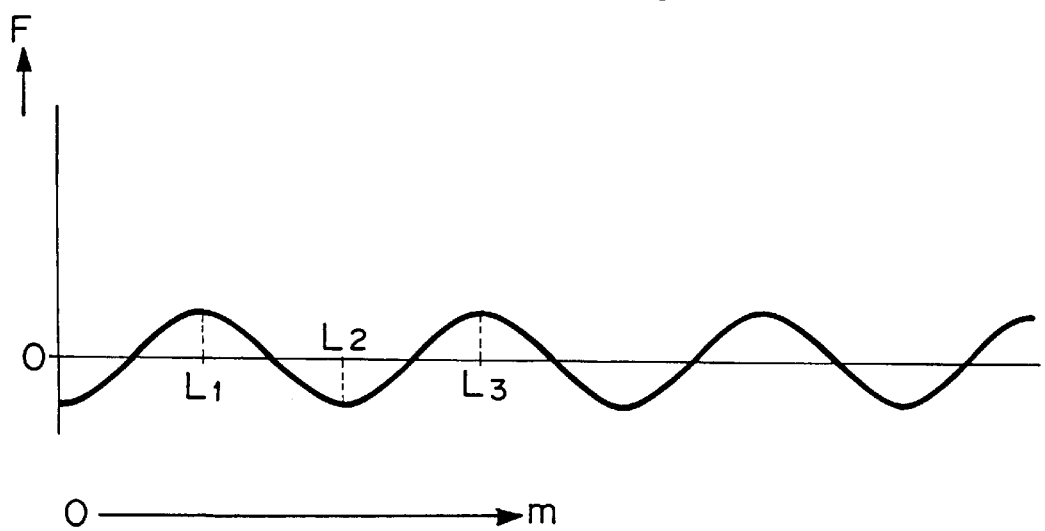
FIG. 13 is a schematic diagram for explaining a fluttering of the vibration vane.

The magnitude of the "fluttering phenomenon" of the tip end of the vibration vane which is induced by the vibration of the vibration vane is varied in accordance with the frequency of the vibration, the length and thickness of the vane, the viscosity and specific gravity of the liquid to be treated, and thus it is preferable to select such length and thickness of the vane as provides most powerful "fluttering" at a given frequency. As the length m (length of a portion extending from the fixing member to the tip) of the vibration vane is varied while the vibrational frequency and the thickness of the vane are kept constant, the magnitude F of the "fluttering" of the vane varies substantially periodically as shown in FIG. 13. It is preferable to select the length $L_1$ providing a first peak or the length $L_2$ providing a second peak as the length m of the vane. One of the length corresponding to the first peak and the length of the second peak is suitably selected in accordance with the requirement that the vibration of the liquid should be magnified or the fluidization of the liquid is intensified. When the length $L_3$ corresponding to a third peak is selected, the amplitude of the vibration is reduced and the application field of the apparatus is somewhat restricted.

The following Table 1 shows an experimental result when the lengths $L_1$ and $L_2$ exhibiting the first and second peaks respectively are obtained at a frequency of 37 Hz to 60 Hz and at 75 W for a vibration vane made of stainless steel as the thickness T thereof is varied.

TABLE 1

| T (mm) | $L_1$ (mm) | $L_2$ (mm) |
|---|---|---|
| 0.10 | about 15 | |
| 0.20 | about 25 | about 70 |
| 0.30 | about 45 | 110–120 |
| 0.40 | about 50 | 140–150 |
| 0.50 | about 55 | |

In this experiment, the length from the center of the vibration rod to the tip end portion of the vibration vane fixing member is set to 27 mm, and the inclination angle α of the vane is set to 15 degrees upwardly.

In the present invention, the vibration rod may be made of plastics.

Figure 14:
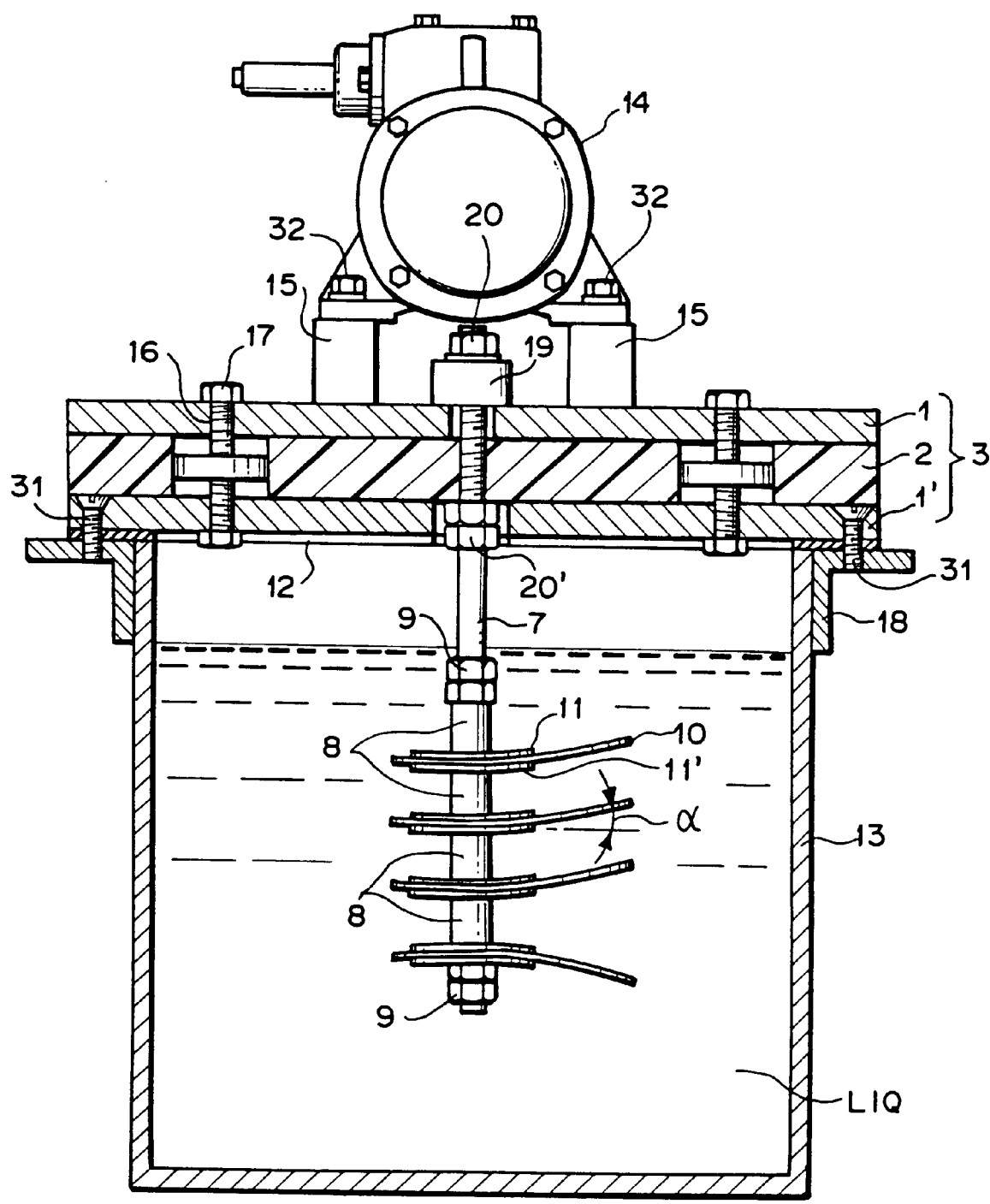
FIG. 14 is a cross-sectional view showing still another embodiment of the apparatus according to the present invention.
Figure 15:
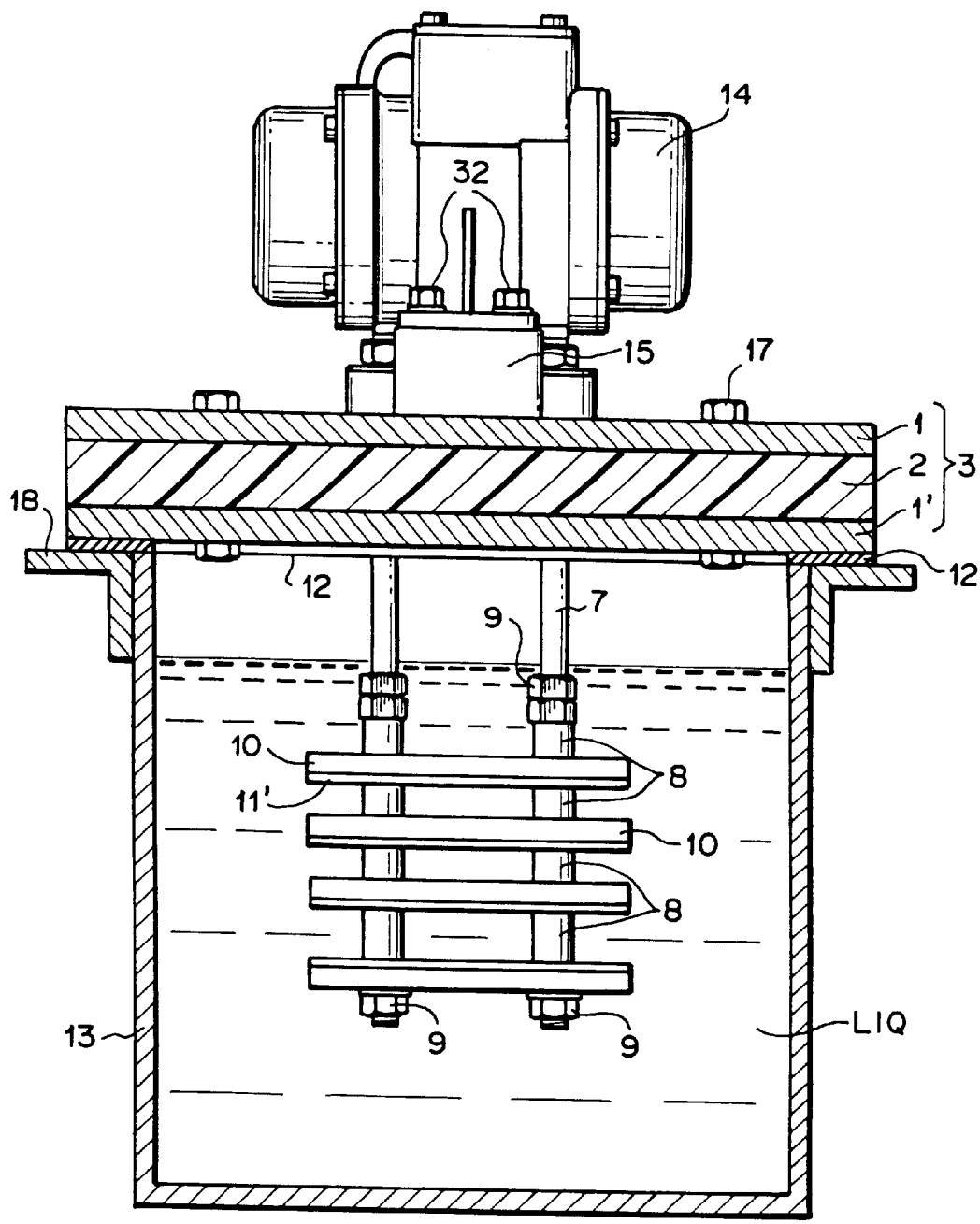
FIG. 15 is another cross-sectional view of the apparatus of FIG. 14.
Figure 16:
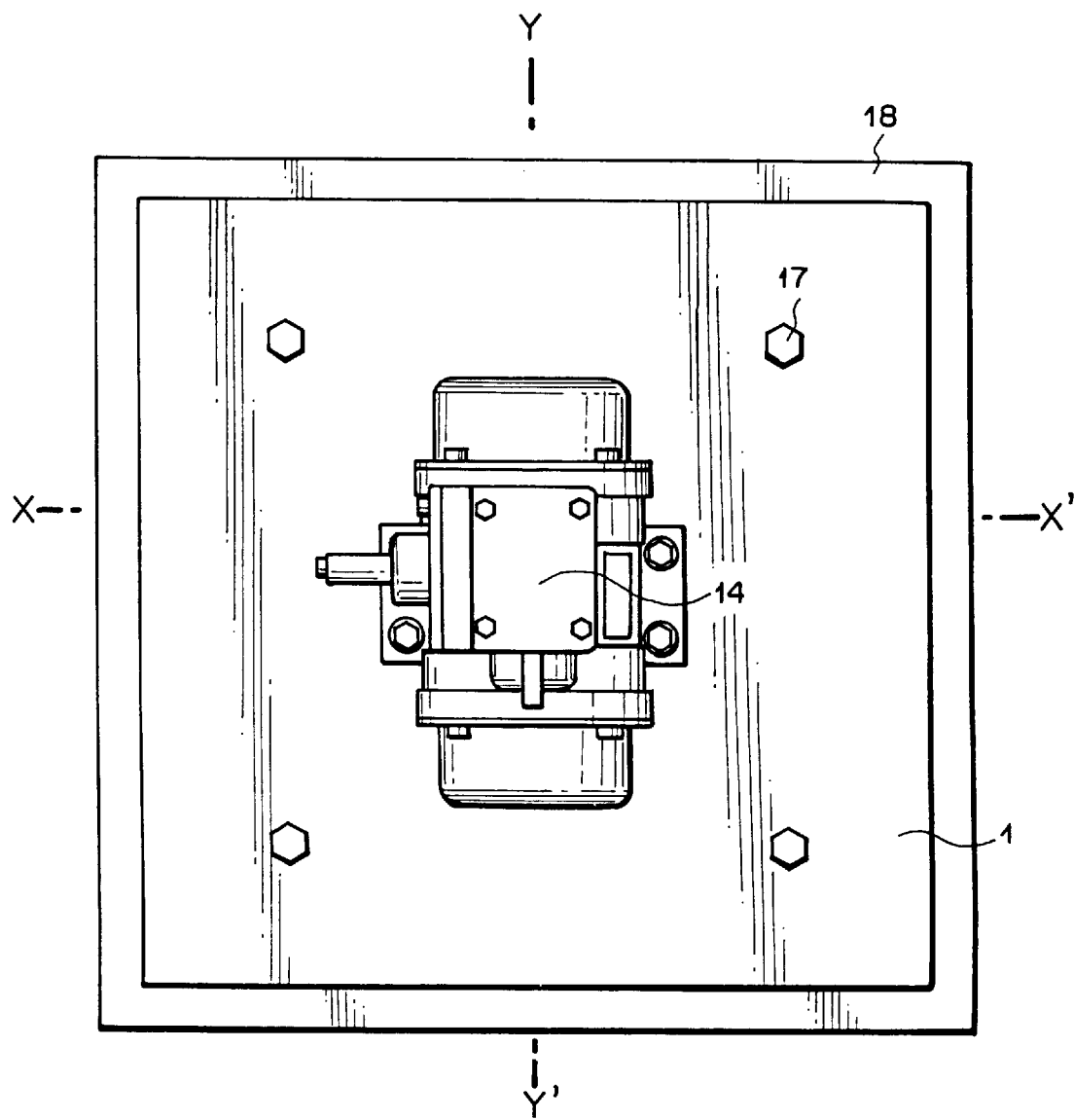
FIG. 16 is a plan view of the apparatus of FIG. 14.

FIGS. 14 and 15 are each a cross-sectional view of an embodiment of the sterilizing apparatus of the present invention, and FIG. 16 is a plan view of this embodiment. FIGS. 14 and 15 are views taken along lines X–X' and Y–Y' of FIG. 16, respectively.

In FIGS. 14 to 16, reference numeral 13 denotes a treatment tank which is charged with liquid LIQ to be treated. Reference numeral 18 denotes a support member fixed to the upper edge of the tank 13. Reference numerals 14 and 15 denote a vibration motor and a vibration motor mount member, respectively. These constitute a vibration generating unit.

Reference numerals 1 and 1' denote an upper metal plate and a lower metal plate, respectively, and reference numeral 2 denotes a rubber plate. These constitute vibration absorbing member 3, which is disposed between the vibration generating unit and the tank 13. The upper and lower metal plates 1, 1' and the rubber plate 2 are fixed by means of bolts 16 and nuts 17 to form a laminate.

The vibration absorbing member 3 is attached to the tank 13 in such a manner that the lower metal plate 1' and the support member 18 are fixed to each other by bolts 31 with packing 12 interposed therebetween. The vibration generating unit is mounted on the vibration absorbing member 3 at a central position thereof away from the support member 18 in such a manner that the vibration motor 14 and the upper metal plate 1 are fixed to each other via the mount member 15 by bolts 32.

Reference numeral 7 denotes a vibrating rod, the upper portion of which is connected to the vibration absorbing member 3 at the central position thereof with use of nuts 20, 20' and rubber ring 19 used as a vibration stress dispersing unit. Reference numeral 10 denote a vibration vane attached to the vibrating rod 7. On the vibrating rod 7, spacers 8 are disposed between the neighboring vibration vanes 10. The vibration vanes 10 each held by upper and lower vibration vane fixing members 11 and 11' are positioned at a certain interval. Reference numeral 9 denotes a nut for holding the spacers 8, vibration vanes 10 and vibration vane fixing members 11, 11' on the vibrating rod 7.

Examples of material of the metal plates 1, 1' are stainless steel, iron, copper, aluminum, suitable alloys, etc. The thickness of the metal plates 1, 1' is 10 to 40 mm for example.

Material of the rubber plate 2 is, for example, synthetic rubber or vulcanized natural rubber, and preferably rubber vibration isolator defined in JIS K6386(1977).

Examples of synthetic rubber are chloroprene rubber, nitrile rubber, nitrile-chloroprene rubber, styrene-chloroprene rubber, acrylonitrile-butadiene rubber, isoprene rubber, ethylene-propylene-diene rubber, epichlorohydrin rubber, alkylene oxide rubber, fluororubber, silicone rubber, urethane rubber, polysulfide rubber, phosphorus rubber (flame-retarded rubber).

Examples of the rubber plate available in market are natural rubber plate, insulating rubber plate, electrically conductive rubber plate, oil-resistant rubber (e.g. NBR), chloroprene rubber plate, butyl rubber plate, chlorinated rubber plate, SBR rubber plate, silicone rubber plate, fluororubber plate, acrylic rubber plate, ethylene-propylene rubber plate, urethane rubber plate, epichlorohydrin rubber plate, fire-retardant rubber plate. It is preferable to use rubber plate made of material having properties of rubber vibration isolator defined in JIS K6386(1977), especially having static modulus of elasticity in shear of 4 to 22 kgf/cm$^2$, preferably 5 to 10 kgf/cm$^2$, and ultimate elongation of 250% or more.

The thickness of the rubber plate 2 is 0.1 mm to 20 mm for example, and preferably 0.5 mm to 10 mm.

FIG. 17A shows a schematic plan view of the vibration absorbing member 3. In FIG. 17A, reference numeral 5 denotes a hole through which the vibrating rod 7 passes. The vibration absorbing member 3 seals the upper opening of the tank 13. The inner diameter of the hole portion of rubber plate 2 which is a part of the hole 5 of the vibration absorbing member 3 is substantially equal to the diameter of the vibrating rod 7, while the inner diameter of a hole of the metal plates 1, 1' which is a part of the hole 5 of the vibration absorbing member 3 is slightly greater than the diameter of the vibrating bar 7 as shown in FIG. 17D.

FIGS. 17B and 17C show a schematic plan view of variations of the vibration absorbing member 3. The vibration absorbing member 3 of FIG. 17B comprises the first portion 3a and the second portion 3b, the facing edges of which are contacted with each other. The vibration absorbing member 3 of FIG. 17C has opening 6 while being positioned on the entirety of the upper edge of the tank 13.

FIGS. 17D and 17E show a cross-sectional view of the vibration absorbing member 3. As shown in FIG. 17E, a flexible sealing member 36 made of soft rubber, etc. may be used to perform perfect seal at a portion where the vibrating rod 7 passes through the opening 5 or 6 of the vibration absorbing member 3. Such a perfect seal is advantageous for preventing contamination of the liquid with external substance such as dust, etc.

Also in case where the flexible sealing member is not used as shown in FIG. 17D, a sufficient seal can be performed on the basis of the function of the rubber plate 2 of the vibration absorbing member 3 in that the expansion and contraction of the rubber plate 2 can follow the motion of the vibrating rod 7 to the considerable extent and the frictional heat thus generated is small.

Figure 18A:
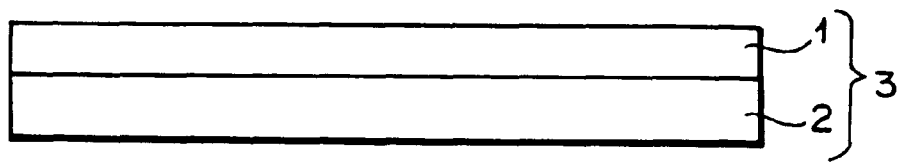
FIGS. 18A to 18E are a front view of the vibration absorbing member.
Figure 18B:
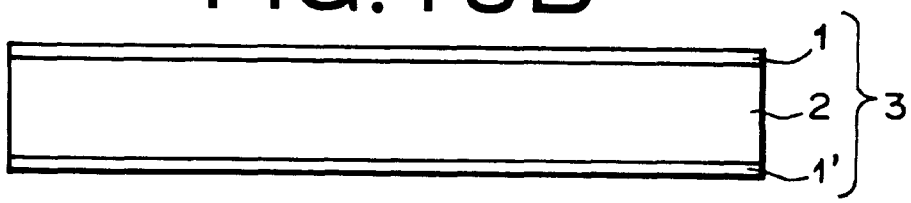
Figure 18C:
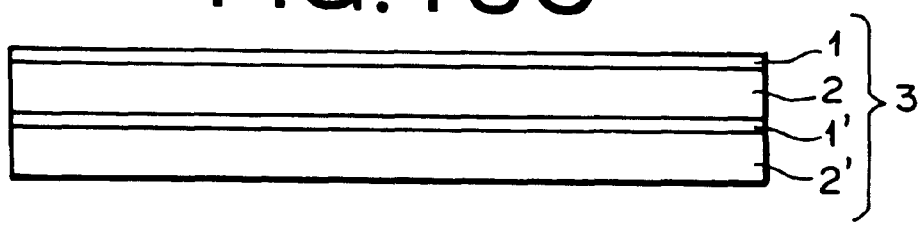
Figure 18D:
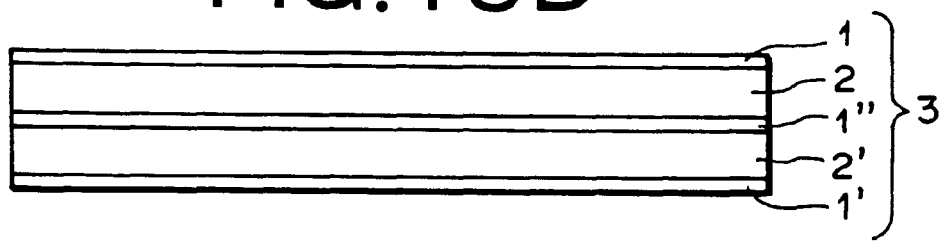
Figure 18E:
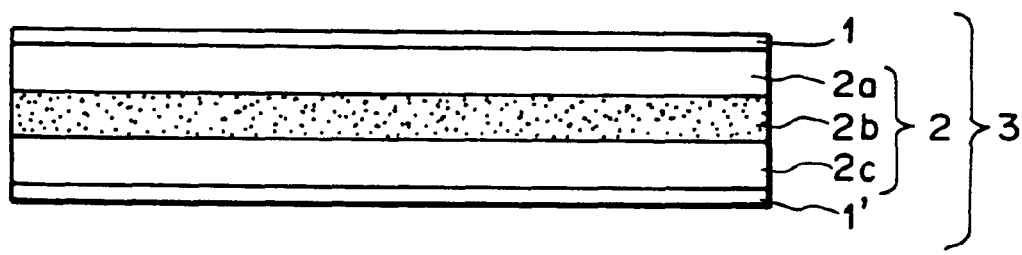

FIGS. 18A to 18E show front view of examples of the vibration absorbing member 3. The vibration absorbing member 3 of FIG. 18B is the same as that of FIGS. 14 and 15. The vibration absorbing member 3 of FIG. 18A comprises metal plate 1 and rubber plate 2. The vibration absorbing member 3 of FIG. 18C comprises upper metal plate 1, upper rubber plate 2, lower metal plate 1' and lower rubber plate 2'. The vibration absorbing member 3 of FIG. 18D comprises upper metal plate 1, upper rubber plate 2, intermediate metal plate 1", lower rubber plate 2' and lower metal plate 1'. The thickness of the intermediate metal plate 1" is 0.3 to 10 mm for example, while the thickness of the upper and lower metal plates 1, 1' is rather large, 10 to 40 mm for example as mentioned above, since the upper metal plate 1 supports the vibration generating unit and the lower metal plate 1' is secured to the support member 18. The vibration absorbing member 3 of FIG. 18E comprises upper metal plate 1, lower metal plate 1', and rubber plate 2 which comprises an upper solid rubber layer 2a, sponge rubber layer 2b and lower solid rubber layer 2c. One of the upper and lower solid rubber layer 2a, 2c may be omitted. Alternatively, a plurality of sponge rubber layers and a plurality of solid rubber layers may be used in the rubber plate. The vibration absorbing member 3 may be formed of a rubber plate.

FIG. 19 shows a partially cross-sectional, perspective view of a variation of the vibration absorbing member 3. It comprises seven rubber plates 2 and six metal plates 1 each being disposed between the adjacent rubber plates 2, and has circular shape. There is provided in the vibration absorbing member 3 a hole 34 through which passes a bolt for securing the member 3 to the treatment tank. The diameter or width W of the member 3 is preferably equal to or greater than twice the thickness T, more preferably three times the thickness T. If the width W is excessively small, the vibration absorbing member 3 is bent retative to the vertical direction and the heat generation becomes remarkably due to the friction between the vibration absorbing member 3 and the bolt.

In the present invention, it is preferable to use the vibration absorbing member 3 including 1 to 10 rubber plates.

The vibration generating unit is preferably attached to the metal plate side of the laminate. The vibration generated by the vibration motor is transmitted to the vibration absorbing member 3 via the mount member 15, or the like. It is preferable to exert pressure due to the weight of the vibration generating unit on the vibration absorbing member 3, especially at an area corresponding to the support member 18 and the upper edge portion of the tank 13, as uniformly as possible.

In the present invention, liquid to be treated may be various kinds of water such as tap water, well water, rainy water, river water, drained water, polluted river water, various kinds of organic solvent polluted with bacteria or the like, or liquid containing inorganic or organic substances.

In the present invention, articles to be treated is not limited to specific ones, and they may contain tableware, parts of food processing apparatus, various bins and containers for food and medical service, medical instruments such as instruments for surgical operations, clothing, bedclothes, fancy goods, vanities, foods such as vegetables/fruits, etc.

When an article to be treated is large and it can be directly set in the treatment tank, it may be directly set in the tank. However, when it is a fancy good or the like, it is preferably set in the tank while put in a porous container or holder such as a cage or the like.

If an article is vibrated, swung or rotated by any means, the contact between the treatment liquid and the article is further enhanced and made uniform irrespective of the size of the article. Therefore, this is preferable. If the article is large, the article itself can be suspended and a suspending member can be vibrated, swung or rotated. If the article is small, the article is put in a porous container and the porous container is vibrated, swung or rotated while the article is fixed in the porous container if necessary. The porous container may be formed of plastic material or metal. It may be formed by forming desired holes in a plastic plate or metal plate. However, if the rate of the open area to the side wall is required to be increased, the side wall is formed of metal wire mesh or metal wire mesh coated with resin. The rate of the open area to the side wall may be set to about 10 to 98%. The number and shape of holes formed in the container are set in conformity with the size and shape of articles to be received and subjected to the strilization treatment in the liquid so as to achieve the highest treatment efficiency. The open area rate is preferably set to 20% or more to the side wall area. If the open area rate is lower than this value, the treatment efficiency is lowered. The horizontally-sectional shape of the container may be circular or polygonal.

The swinging operation for the articles performed in the present invention means such a slow swing motion that the swing amplitude is equal to about 10 to 100 mm, preferably 20 to 60 mm and the swinging frequency is equal to about 10 to 60 per minute. If the rotating operation is carried out, the same effect can be sufficiently obtained by carrying out the rotation at a rotating number of about 10 to 60 per minute.

Figure 20:
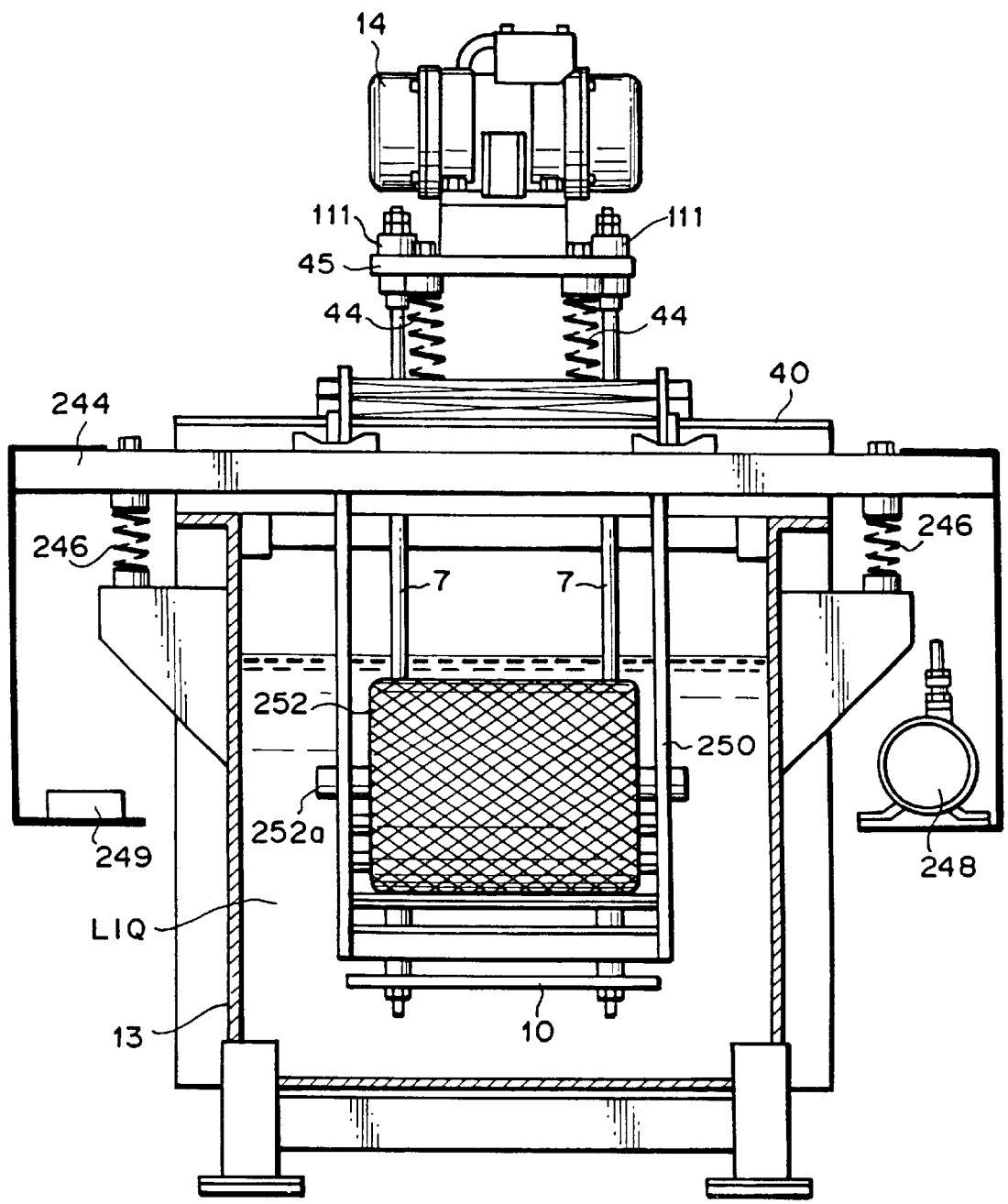
FIG. 20 is a cross-sectional view showing still another embodiment of the apparatus according to the present invention.

FIG. 20 is a cross-sectional view of an embodiment of a sterilizing apparatus having such a porous container for holding the articles and a driving means for moving the container.

In FIG. 20, a vibration generating unit containing the vibration motor 14 is mounted on the treatment tank 13 in the same manner as the apparatus of FIGS. 9 to 11. In addition, a vibration frame 244 is attached to the treatment tank 13 via coiled springs 246 used for absorbing the vibration. A vibration motor 248 and a balance weight 249 are secured to the vibration frame 244. The container 252 is attached to the vibration frame 244 via connecting members 250, and is rotated around an axis 252a by means of a motor (not shown) controlled by an inverter (not shown).

The articles to be treated are taken in the container 252 which is rotated around the axis 252a and vibrated by the vibration energy generated in the vibration motor 248 and transmitted through the frame 244 and connecting members 250, so that the articles are vibrated and rolled in the container 252.

The swing motion of the articles can be performed if the lower ends of the above coiled springs 246 are secured to a member which is attached to the treatment tank 13 and is reciprocally moved by means of a motor (not shown).

It is possible to arrange the container 252 so that the axis 252a extends in vertical direction.

The bacteria to be exterminated in the sterilization are not limited to specific ones, however, the present invention is particularly effective to at least coliform bacteria (*Colon bacillus*, Enteropathogenic *Escherichia coli*, 0–157), Salmonella, *Vibrio parahaemolyticus*, Campylobacter, Yersinia, *Welch bacillus*, NAG vibrio, *Pseudomonas aeruginosa, Burkholderia cepacia, Staphylococcus aureus, Staphylococcus epidermidis, Streptococcus pneumoniae,* Serratia, Proteus, Enterobacter, Citrobacter, Enterococcus, Klebsiella, Bacteroides, Legionella, Mycobacterium, *Pneumocystis carinii,* fungus, pathogenic virus, etc.

Metals such as Ag, Pd, Au, Pt, Ni, Cu, Zn, Sb, Mg, Sn, Pb, etc. may be used as the sterilizing metal or bactericidal metal for material of the vibration vane or vibration vane fixing member. These metals may be used alone or as alloy thereof (for example, brass) or alloy of these metals and other metals. Further, metallic oxides such as titanium oxide ($TiO_2$), zinc oxide (ZnO), silver oxide, copper oxide, etc. may be used as the sterilizing metallic compound or bactericidal metallic compound for material of the vibration vane or vibration vane fixing member. The sterilizing metallic oxide may have a form of particle. The size of the particles is not limited to a specific value. However, it is preferable that the diameter of particles is as small as possible because the surface area of the particles is increased, and the particle diameter is preferably set to 5 $\mu$m or less.

The surface of the vibration vane or vibration vane fixing member formed of a sterilizing metal or a sterilizing metallic compound such as a metallic oxide or the like can be prepared by plating the sterilizing metal or its alloy on a substrate for the vibration vane or vibration vane fixing member, or by performing composite-plating of particles containing the sterilizing metal component or particles of the sterilizing metallic compound on the substrate. The formation method of the surface layer as described above may be applied to the vibration vane and the vibration vane fixing member formed of plastic materials. In this case, a plastic substrate is subjected to a normal surface treatment in order to enhance adhesion properties as described in "Handbook of Plating Technique" pp650 to 664 issued on Jul. 25, 1971 by Nikkan Kogyo Shinbun Company, and then plating such as silver plating or the like or composite plating is carried out.

In the composite-plating, Ni, Cu, Co, Au, Cr, Ag, Fe, Pb, etc. are used as matrix matrial, and metallic oxide, metallic carbide, metallic nitride, etc. are used as particle material. In the present invention, at least one of the matrix matrial and the particle material is sterilizing or bactericidal. Especially, it is preferable to use the combination of bactericidal titanium oxide particles and matrix of bactericidal Ni, Cu, Au, Pb, or the like.

As the sterilizing metallic compound, sterilizing stainless steel containing Ag or Ni as a component thereof may be used. As the sterilizing matallic compound, titanium oxide film formed by surface oxidation treatment, for example electrolytic oxidation or anodization, of titanium member or titanium alloy member may be also used. In order to achieve higher sterilizing activity based on higher photocatalytic activity of the titanium oxide film, it is preferable to form the titanium oxide film as follows: First, porous anodic oxide film on titanium plate is prepared in a mixture of $H_3PO_4$, $H_2SO_4$ and $H_2O_2$ with a voltage higher than spark discharge (first anodization). Then, low valent titanium oxides formed in the first anodized film, which deactivate photocatalytic properties, are removed by reanodization in the mixture $NH_4HF_2$ and $H_2O_2$ (second anodization). $TiO_2$ particles are added to the mixture of $H_3PO_4$, $H_2SO_4$ and $H_2O_2$ for the improvement of the photocatalytic activity of the anodized film. As the sterilizing matallic compound, aluminum oxide film formed by surface oxidation treatment of aluminum member or aluminum alloy member or magnesium oxide film formed by surface oxidation treatment of magnesium member or magnesium alloy member may be also used. With use of the above sterilizing matallic compound in combination with ultraviolet-light irradiation mentioned later, sterilizing activity of the vibration vane and the vibration vane fixing member can be greatly enhanced.

The thickness of the surface layer thus prepared is not limited to a specific value, however, the thickness of about 5 to 20 $\mu$m can normally bring a sufficient effect. As occasion demands, the overall vibration vane may be formed of sterilizing metal or any metal dispersed with sterilizing metal particles.

If magnetic field generating materials are used for the vibration vanes or the vibration vane fixing members, water to be treated is activated and sterilized. If the treated water is used to clean clothes, it has been found that the water is activated to the extent that the amount of cleaning agent to be used can be saved to $\frac{1}{5}$.

In order to enable the vibration vanes or the vibration vane fixing members including accessories thereof such as the stopper rings, the bolts, the nuts, etc. to generate magnetic field or magnetic force, any magnetic field generating means may be used. For example, permanent magnet (hard magnetic material) may be used, or electromagnet may be used. As occasion demands, soft magnetic material may be used. As the hard magnetic material may be used ferrite magnetic material, rare earth magnetic material, magnetic steel or the like. Specifically, Alnico magnet, samarium cobalt magnet, neodymium magnet, iron magnet, boron magnet or the like may be used. In the case of the soft magnetic material, a coil is wound around the soft magnetic material, and necessary magnetization is induced in the soft magnetic material (soft magnetic material is magnetized) each time on the basis of the principle of the electromagnet by making current flow through the coil. Soft iron, silicon steel, Permalloy or the like may be used as the soft magnetic material. When the soft magnetic material is magnetized on the basis of the principle of the electromagnet, the polarity may selectively set to plus or minus like (1) it is varied from plus to minus, (2) it is varied from minus to plus, (3) all is set to minus, (4) all is set to plus, or (5) specific vanes are set to plus while the other specific vanes are set to minus. These magnetic materials may be flexible thin plate magnet as disclosed in Japanese Utility Model Publication No. Sho-53-21438. The intensity of the magnetic field is preferably equal to 500 oersted or more.

These magnetic materials are preferably used particularly for the vibration vane fixing members including the accessories thereof such as the stopper rings, the bolts, the nuts, etc.

With these materials, bacteria such as *Colon bacillus,* 0–157, Salmonella, Streptococcus, etc. can be extremely effectively captured.

The substrate or base member of the vibration vanes and the vibration vane fixing members may be made of the magnetic materials as described above, however, magnetic rubber may be used while adhering to the substrate of the vibration vanes or the vibration vane fixing members. If no magnetic material is required, any metal material or plastic material may be used for the substrate. Further, magnetic powder or rare earth magnetic powder may be contained in the substrate.

It is preferable that the liquid to be treated is vibrationally stirred so as to have the flow rate of 100 mm/sec or more when detected by three dimensional electromagnetic flow-meter (ACM300-A: available from Alec Electronics Co., Ltd.).

The sterilization activity of the vibration vane and the vibration vane fixing member is enhanced by irradiating them with ultraviolet right.

Figure 21:
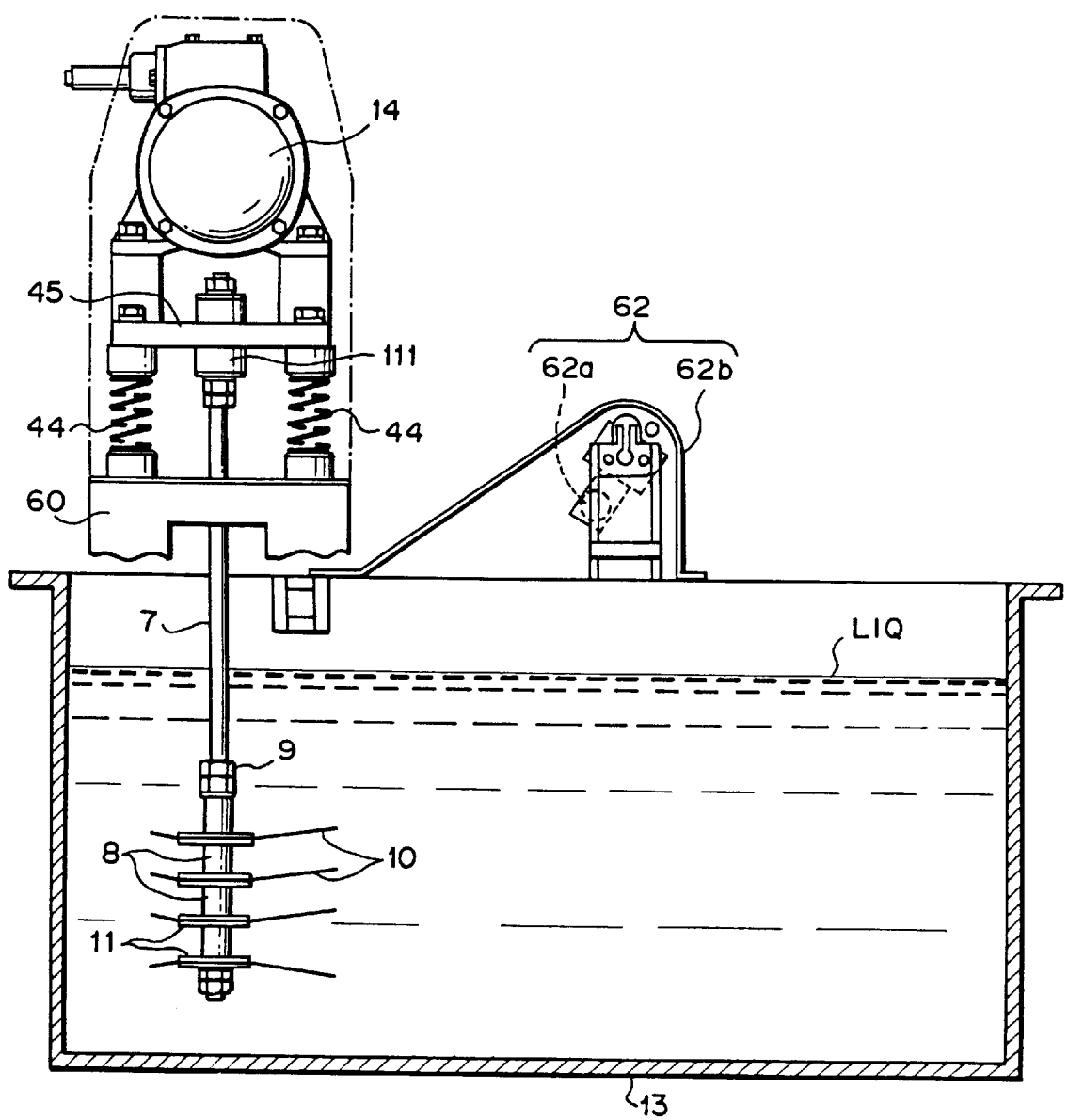
FIG. 21 is a cross-sectional view showing an embodiment of a sterilizing apparatus containing an ultraviolet-light irradiating device according to the present invention.
Figure 22:
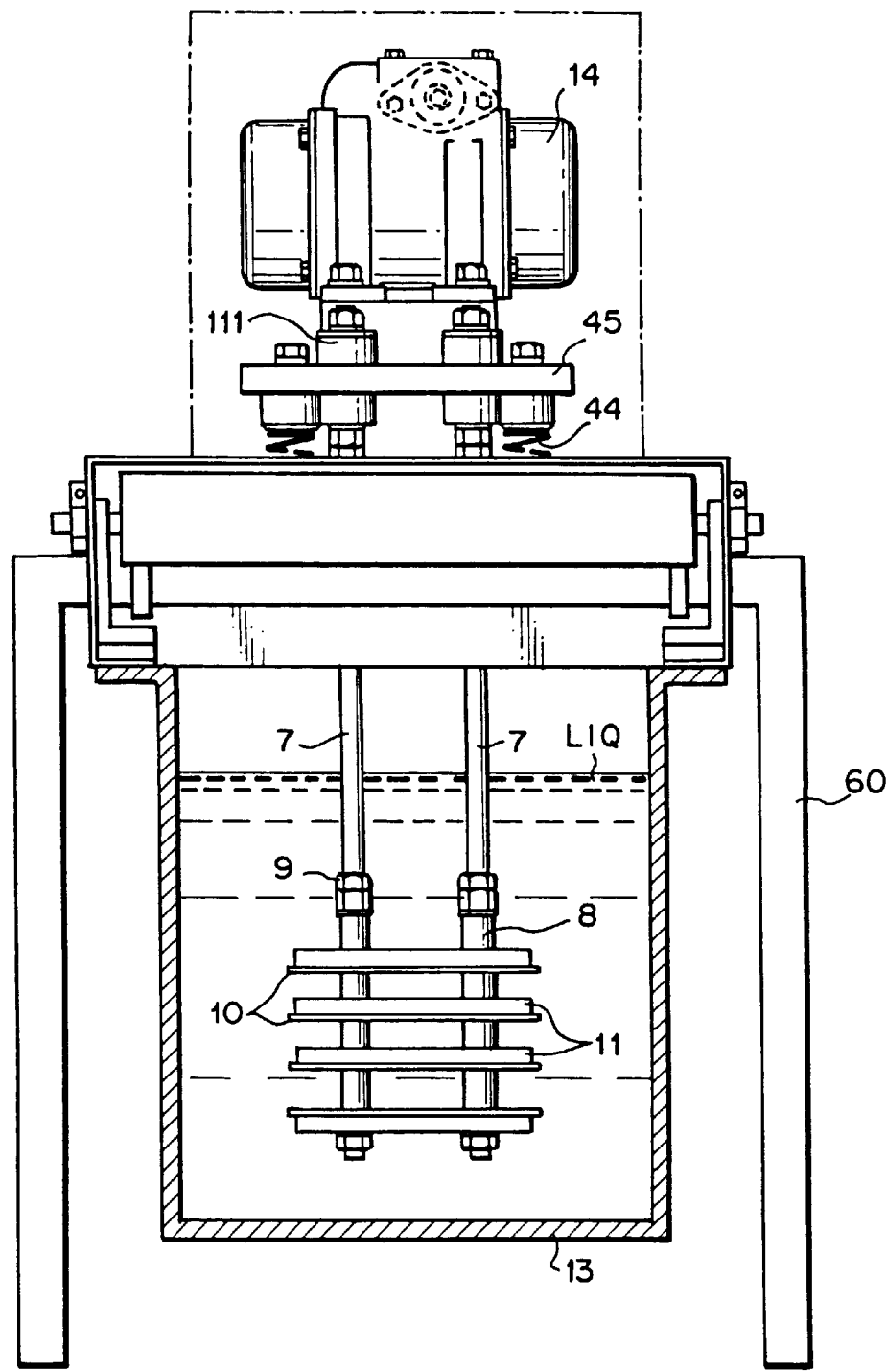
FIG. 22 is a cross-sectional view of the apparatus of FIG. 21.

FIGS. 21 and 22 show an embodiment of the present invention in which ultraviolet-light irradiation is used. In this embodiment, the vibrationally stirring apparatus is not mounted on the treatment tank 13, but mounted on a base member 60. An ultraviolet-light irradiating device 62 attached to the upper edge of the treatment tank 13 has an ultraviolet lamp 62a and a reflecting cover 62b. As the ultraviolet lamp 62a, the following lamps are preferably used: Deuterium lamp; Xenon lamp; Mercury lamp; High pressure mercury lamp; Super high pressure mercury lamp; Germicidal lamp; Blacklight lamp.

Wavelength of ultraviolet light of the lamp 62a is 200 to 400 nm for example, preferably 200 to 300 nm. High pressure mercury lamp of 253.7 nm central wavelength is most preferably used.

The ultraviolet lamp 62a of 10 to 40 W is used alone or in plurality. The lamp 62a is disposed at a position in the upper right direction relative to the vibration vane 10, and extends horizontally. The reflecting cover 62b has such a shape that the ultraviolet light reflected by the inner surface of the cover 62b advances to the vibration vane 10. The reflecting cover 62b also functions to prevent the leak of the ultraviolet light toward the outside of the sterilizing apparatus.

In the apparatus of this embodiment, the liquid LIQ is vibrationally stirred by the vibration vane 10 while irradiating the vibration vane 10 and/or vibration vane fixing member (11, etc.) with the ultraviolet-light. The activity of the sterilizing metal or sterilizing metallic compound is enhanced by the ultraviolet-light irradiation to reduce the treatment time. It is considered that the above effect of the ultraviolet-light irradiation is based on the activation of the sterilizing metal or sterilizing metallic compound by the ultraviolet light, resulting in longer sustenance of the sterilization effect as compared with a case without use of the ultraviolet-light irradiation.

Figure 23:
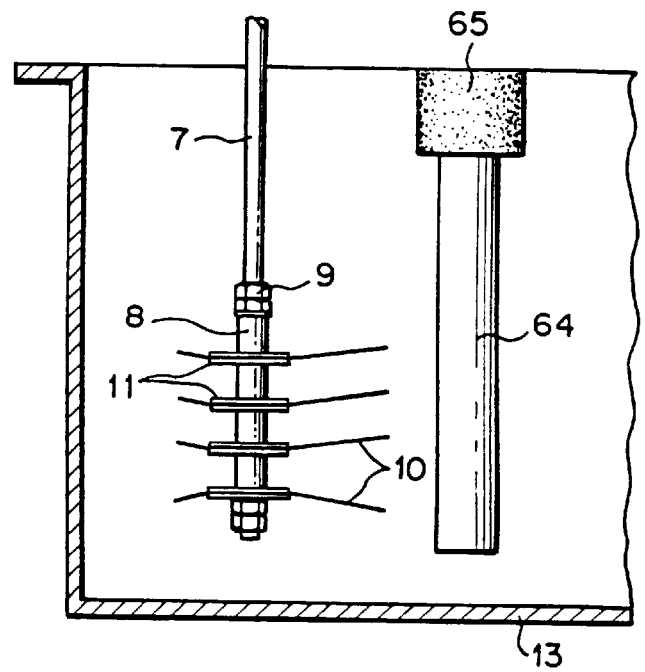
FIG. 23 is a partial, cross-sectional view showing another embodiment of a sterilizing apparatus containing an ultraviolet-light irradiating device according to the present invention.
Figure 24:
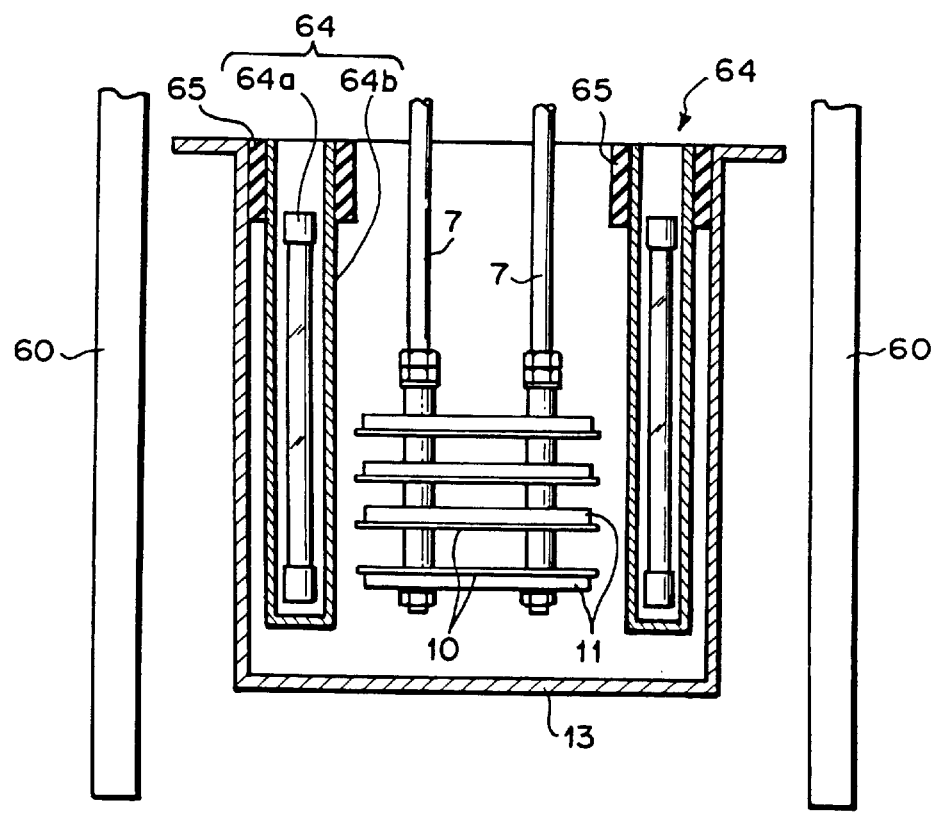
FIG. 24 is a partial, cross-sectional view of the apparatus of FIG. 23.

FIGS. 23 and 24 show another embodiment of the present invention in which ultraviolet-light irradiation is used. In this embodiment, an ultraviolet-light irradiating device 64 is disposed at the inside of the treatment tank 13. The device 64 has ultraviolet lamp 64a and protection tube 64b for accommodating the lamp 64a therein which is made of ultraviolet-transmitting material. The protection tube 64b extends in vertical direction, positions in the neighborhood of the vibration vane 10, and is held by a clamping member 65 attached to the inner surface of the treatment tank 13. The protection tube 64b made of quartz, pyrex or transparent polyvinyl alcohol are preferably used. The protection tube 64b may be integrated into the lamp 64a.

According to this embodiment, the ultraviolet lamp 64a can be disposed at the position closer to the vibration vane 10 as compared with the embodiment of FIGS. 21 and 22.

The present invention will be described in more detail with the following examples, however, the present invention is not limited to the following examples.

EXAMPLE 1

An apparatus of FIGS. 9 to 11 was used, in which the vibration vane was made of magnetic steel having a coated surface layer of silver. The size of the vane was 210 mm×140 mm×0.6 mm. The vibration vane fixing member was made of ferromagnetic material of neodymium magnet. The size of the fixing member was 210 mm×60 mm×4 mm. The vibration motor was 200 V, 250 W, 3-phase.

The inner size of the treatment tank was 450 mm×1100 mm×500 mm. As the liquid to be treated was used the potable water containing the following bacteria:

General bacteria . . . 1000 n/ml

Coliform bacteria . . . 9500 MPN/100 ml

Detecting of the bacteria was performed according to the microorganism test method described in "Manual of Test Method for Potable Water" (1993) published by Nippon Suido Kyokai, especially for general bacteria and coliform bacteria (pp483 to 492). n is the number of bactera, and MPN is the most probable number determined by MPN (Most Probable Number) method as described in the above "Manual of Test Method for Potable Water" (pp475 to 480).

The treatment liquid was poured into the treatment tank. The vibration motor was operated by the inverter at a frequency of 40 Hz at a room temperature. The amplitude of the vibration vane was 0.15 mm and the vibrational frequency of the vane was 800 times per minute. Flow rate of the treatment liquid detected by the three dimensional electromagnetic flowmeter (ACM300-A) at a position separated by 3 cm from the tip end of the vibration vane was 200 mm/sec in each of X, Y and Z directions. The flow rate was detected in the same apparatus as that used in this Example except that magnetic members were replaced by non-magnetic members.

The results of the sterilization are shown in the following Table 2.

TABLE 2

| Treatment time (min.) | 0 | 1 | 2 | 3 | 5 | 10 |
| --- | --- | --- | --- | --- | --- | --- |
| General bacteria (n/ml) | 1000 | 500 | 200 | 20 | undetected | undetected |
| Coliform bacteria (MPN/100 ml) | 9500 | 4800 | 1600 | 150 | undetected | undetected |

EXAMPLE 2

Cut rose flowers were arranged in a vase filled with water. In case of the water treated for 5 minutes in Example 1 the flowers drooped after 10 days, while in case of non-treated water used in Example 1 the flowers drooped after 5 days.

EXAMPLE 3

The test was conducted in the same manner as Example 1 except that the vibration vane was made of stainless steel having a coated surface layer of silver, and, as the liquid to be treated was used the river water containing the following bacteria:

General bacteria . . . 1500 n/ml

Coliform bacteria . . . 9600 MPN/100 ml

The results of the sterilization are shown in the following Table 3.

TABLE 3

| Treatment time (min.) | 0 | 10 | 30 | 60 | 90 |
|---|---|---|---|---|---|
| General bacteria (n/ml) | 1500 | 500 | undetected | undetected | undetected |
| Coliform bacteria (MPN/100 ml) | 9600 | 8000 | 5000 | 1600 | 200 |

EXAMPLE 4

An apparatus of FIGS. 9 to 11 was used, in which the vibration vane was made of stainless steel having a coated surface layer of silver formed on a pre-coated layer. The size of the vane was 210 mm×140 mm×0.6 mm. The vibration vane fixing member was made of ferromagnetic material of neodymium magnet. The size of the fixing member was 210 mm×60 mm×4 mm. The vibration motor was 200 V, 150 W, 3-phase. The angle α was 0 degree.

The inner size of the treatment tank was 450 mm×1100 mm×500 mm. As the liquid to be treated was used water inoculated with Coliform bacteria of $2.4 \times 10^3$ CFU/ml. CFU is the number of colony forming unit counted according to CFU (Colony Forming Unit) agar-plate test. The test was conducted by Analytical Technical Laboratory of Japan Oilstuff Inspectors' Corporation (Nippon Yuryo Kentei Kyokai), located at Yokohama, Japan.

The treatment liquid was poured into the treatment tank. The vibration motor was operated by the inverter at a frequency of 40 Hz at a room temperature. The amplitude of the vibration vane was 0.15 mm, and the vibrational frequency of the vane was 800 times per minute. Flow rate of the treatment liquid detected as the same manner as Example 1 was 200 mm/sec in each of X, Y and Z directions.

For comparison, CFU was counted for the water taken in the treatment tank while the vibrationally stirring apparatus was omitted.

The results of the sterilization are shown in the following Table 4.

TABLE 4

| | Number of Live Bacteria (CFU/ml) Vibrationally Stirring Apparatus | |
|---|---|---|
| Treatment time (hour) | Used | Not used |
| 0 | $5.0 \times 10$ (*) | $1.8 \times 10^3$ |
| 1 | 0 | $2.2 \times 10^3$ |
| 2 | 0 | $2.4 \times 10^3$ |
| 3 | 0 | $2.6 \times 10^3$ |
| 4 | 0 | $2.1 \times 10^3$ |
| 5 | 0 | $2.5 \times 10^3$ |
| 6 | 0 | $1.8 \times 10^3$ |
| 7 | 0 | $2.0 \times 10^3$ |
| 8 | 0 | $1.7 \times 10^3$ |

(*) the vibrationally stirring apparatus was operated for 3 minutes in order to disperse bacteria in the water.

EXAMPLE 5

The test was conducted in the same manner as Example 4 except that as the liquid to be treated was used water inoculated with *Salmonella enteritidis* of $7.5 \times 10^3$ CFU/ml.

The results of the sterilization are shown in the following Table 5.

TABLE 5

| | Number of Live Bacteria (CFU/ml) Vibrationally Stirring Apparatus | |
|---|---|---|
| Treatment time (min.) | Used | Not used |
| 0 | $7.3 \times 10^3$ | $6.8 \times 10^3$ |
| 1 | $4.8 \times 10^3$ | NT (**) |
| 3 | $2.4 \times 10^3$ | NT |
| 5 | $2.2 \times 10^3$ | $6.0 \times 10^3$ |
| 10 | $1.2 \times 10^3$ | $4.7 \times 10^3$ |
| 20 | $2.8 \times 10$ | NT |
| 30 | $2.4 \times 10$ | $4.7 \times 10^3$ |
| 60 | 0 | $4.1 \times 10^3$ |
| 120 | 0 | $4.0 \times 10^3$ |

(**) NT: not tested

EXAMPLE 6

The test was conducted in the same manner as Example 4 except that as the liquid to be treated was used water inoculated with Enterohaemorrhagic *E. coli* 0–157 of $2.6 \times 10^3$ CFU/ml.

The results of the sterilization are shown in the following Table 6.

TABLE 6

| | Number of Live Bacteria (CFU/ml) Vibrationally Stirring Apparatus | |
|---|---|---|
| Treatment time (min.) | Used | Not used |
| 0 | $2.6 \times 10^3$ | $2.6 \times 10^3$ |
| 1 | $1.5 \times 10^3$ | NT |
| 3 | $1.5 \times 10^2$ | NT |
| 5 | $1.5 \times 10^2$ | $2.9 \times 10^3$ |
| 10 | $1.1 \times 10^2$ | $2.8 \times 10^3$ |
| 20 | $2.5 \times 10$ | NT |
| 30 | 0 | $2.9 \times 10^3$ |
| 60 | 0 | $2.9 \times 10^3$ |
| 120 | 0 | $2.8 \times 10^3$ |

EXAMPLE 7

The apparatus used in Example 4 was used. In the treatment liquid in the treatment tank, 30 dishes each having a diameter of about 25 cm as the solid articles to be treated were submerged while vertically arranged in parallel to each other in a cage made of wire mesh. The articles were (A) 10 dishes made of glass, (B) 10 dishes made of aluminum and (C) 10 dishes made of anodized aluminum.

Sterilization treatment for 5 minutes was conducted repeatedly at the repetition number shown in Tables 7 and 8, which show the results of the sterilization. Rate of removing bacteria was determined. Table 7 concerns the case where the treatment liquid was sterilized, distilled water, while Table 8 concerns the case where the treatment liquid was sterilized, distilled water containing 0.25 wt % of cleaning agent for tableware.

TABLE 7

| | Bacteria Removing Rate (%) Vibrationally Stirring Apparatus | | | | | |
|---|---|---|---|---|---|---|
| | Used | | | Not used | | |
| Repetition Number | A | B | C | A | B | C |
| 1 | 99.5 | 97.5 | 95.1 | 38.8 | 18.5 | 16.4 |
| 2 | 100 | 100 | 100 | 40.9 | 27.7 | 21.8 |
| 3 | 100 | 100 | 100 | 34.4 | 31.3 | 27.5 |
| 4 | | | | 41.7 | 43.7 | 29.6 |
| 5 | | | | 42.4 | 42.6 | 19.4 |
| 6 | | | | 39.0 | 29.4 | 28.9 |
| 7 | | | | 37.6 | 25.2 | 30.3 |
| 8 | | | | 39.2 | 38.1 | 25.9 |
| 9 | | | | 34.8 | 29.5 | 29.0 |
| 10 | | | | 43.1 | 27.6 | 35.2 |

TABLE 8

| | Bacteria Removing Rate (%) Vibrationally Stirring Apparatus | | | | | |
|---|---|---|---|---|---|---|
| | Used | | | Not used | | |
| Repetition Number | A | B | C | A | B | C |
| 1 | 100 | 100 | 100 | 88.5 | 76.4 | 70.4 |
| 2 | 100 | 100 | 100 | 90.4 | 76.3 | 62.6 |
| 3 | | | | 88.3 | 66.3 | 67.3 |
| 4 | | | | 87.6 | 76.5 | 71.2 |
| 5 | | | | 92.9 | 56.5 | 65.4 |
| 6 | | | | 90.1 | 60.9 | 66.9 |
| 7 | | | | 94.1 | 56.2 | 71.1 |
| 8 | | | | 90.1 | 84.6 | 69.4 |
| 9 | | | | 93.1 | 78.3 | 59.6 |
| 10 | | | | 91.9 | 80.0 | 85.2 |

EXAMPLE 8

The apparatus used in Example 4 was used. In the treatment liquid in the treatment tank, 20 dishcloths made of cotton each having a size of 20 cm×40 cm as the solid articles to be treated were submerged while accomodated in a cage made of wire mesh. The dishcloths were polluted by Coliform bacteria.

Sterilization treatment was conducted for 30 minutes. The treatment liquid was (X) sterilized, distilled water, or (Y) sterilized, distilled water containing 0.25 wt % of cleaning agent for tableware. The number of Coliform bacteria was determined before and after the treatment. For comparison, the same treatment liquids and treatment articles were subjected to washing treatment with the conventional washing machine.

The results of the sterilization are shown in the following Table 9.

TABLE 9

| | Number of Coliform Bacteria | |
|---|---|---|
| | X | Y |
| Before Treatment | $42 \times 10^5$ | $42 \times 10^5$ |
| After Treatment | | |
| [a] Present Invention | 0 | 0 |
| [b] Washing with Washing machine | $26 \times 10^5$ | $18 \times 10^4$ |

EXAMPLE 9

An apparatus of FIGS. 21 and 22 was used to conduct the sterilization treatment, in which the vibrationally stirring apparatus was as follows:

Vibration motor: 150 W, 200 V, 3-phase

Vibration vane: 210 mm×140 mm×0.6 mm in size, made of stainless steel having a coated surface layer of silver of 15 μm in thickness; four vanes were used.

Vibration vane fixing member: (1) 210 mm×60 mm×4 mm in size, made of neodymium magnet; two fixing members were disposed at both sides of one vane. (2) 210 mm×60 mm×4 mm in size, made of stainless steel; six fixing members were used, each two members being disposed at both sides of each of the other vanes.

Teflon sheets were interposed between the vibration vane and the corresponding fixing members.

The inner size of the treatment tank made of heat-resistant polyvinyl chloride was 400 mm×700 mm×450 mm. The treatment tank may be made of stainless steel.

An ultraviolet lamp (GL-20: manufactured by Toshiba Corporation, 20 W, length of 250 mm, central wavelength of 253.7 nm) was used. The interval between the lamp and the vibration vanes was 200 to 300 mm.

The vibration motor was operated at 40 Hz under the frequency control by the inverter. The amplitude of the vibration vane was 0.15 mm, and the vibrational frequency of the vane was 800 times per minute. Flow rate of the treatment liquid (liquid to be treated) was 200 mm/sec in each of X, Y and Z direstions.

As the liquid to be treated, pure water into which bacteria was added was used.

The ultraviolet-light irradiation was performed with the ultraviolet lamp turned on [Case 9-A].

The result of the sterilization are shown in the following Table 10. The detection of the bacteria was performed according to membrane filter method (MF method) with use of Milliflex-100 Test System available from Nippon Millipore Corporation.

For comparison, the tests were conducted for a case where the treatment was performed without the ultraviolet lamp turned on [Case 9-B], and another case where the treatment was performed with the ultraviolet lamp turned on while stirring the treatment liquid with the conventional screw type stirrer instead of the vibrationally stirring apparatus of the present invention [Case 9-C].

TABLE 10

| Treatment time (min.) | 0 | 10 | 30 | 60 | 120 | 180 |
|---|---|---|---|---|---|---|
| Case 9-A (n/ml) | 600 | 0 | 0 | 0 | 0 | 0 |
| Case 9-B (n/ml) | 600 | 200 | 150 | 100 | 100 | 100 |
| Case 9-C (n/ml) | 600 | 500 | 450 | 400 | 350 | 350 |

When the treatment liquid was taken on a shallow dish, and subjected to the ultraviolet-light irradiation by the above ultraviolet lamp, the number of the bacteria was reduced to about 200 n/ml with 60-minutes treatment, however, no more reduced thereafter.

EXAMPLE 10

The test was conducted in the same manner as Example 9 except that the following: As the vibration vane, 0.6 mm thick titanium plate having a titanium oxide surface layer of golden color was used. The vibration vane was formed by electrolytic oxidation treatment under the condition of electrolyte of 15% sulfuric acid; temperature of 20° C.; voltage of 3 V; treatment time of 5 minutes. The vibration vane fixing members made of neodymium magnet were used for one vane, and the vibration vane fixing members made of titanium were used for the other three vanes. As the liquid to be treated, carbonated beverage into which Coliform bacteria was added was used [Case 10-A].

The result of the sterilization are shown in the following Table 11.

For comparison, the test was conducted for a case where the treatment was performed without the ultraviolet lamp turned on [Case 10-B].

TABLE 11

| Treatment time (min.) | 0 | 10 | 30 | 60 | 120 | 180 |
|---|---|---|---|---|---|---|
| Case 10-A (n/ml) | 5000 | 200 | 30 | 0 | 0 | 0 |
| Case 10-B (n/ml) | 5000 | 3000 | 600 | 600 | 500 | 400 |

EXAMPLE 11

The test was conducted in the same manner as Example 10 except that the following: The ultraviolet-light irradiating device of FIGS. 23 and 24 was used, in which two ultraviolet lamps were used. As the liquid to be treated, milk into which Enterohaemorrhagic *E. Coli* 0–157 was added was used [Case 11-A].

The result of the sterilization are shown in the following Table 12.

For comparison, the test was conducted for a case where the treatment was performed without operating the vibrationally stirring apparatus while the ultraviolet lamp was turned on [Case 11-B].

TABLE 12

| Treatment time (min.) | 0 | 10 | 30 | 60 | 120 | 180 |
|---|---|---|---|---|---|---|
| Case 11-A (n/ml) | 3000 | 500 | 100 | 0 | 0 | 0 |
| Case 11-B (n/ml) | 3000 | 3000 | 2000 | 2000 | 1500 | 1500 |

It can be understood that rapid and sufficient sterilization can be achieved by performing both the vibrationally stirring and the ultraviolet-light irradiation, whereas the sterilizing effect is relatively low when the ultraviolet-light irradiation was conducted without performing the vibrationally stirring.

EXAMPLE 12

The test was conducted in the same manner as Example 10 except that the following: The vibration vane made of sterilizing stainless steel was used. As the liquid to be treated, juice having chemical activity to silver into which Coliform bacteria was added was used [Case 12-A].

The result of the sterilization are shown in the following Table 13.

For comparison, the test was conducted for a case where the treatment was performed without operating the vibrationally stirring apparatus while the ultraviolet lamp was turned on [Case 12-B].

TABLE 13

| Treatment time (min.) | 0 | 10 | 30 | 60 | 120 | 180 |
|---|---|---|---|---|---|---|
| Case 12-A (n/ml) | 50000 | 4000 | 200 | 0 | 0 | 0 |
| Case 12-B (n/ml) | 50000 | 50000 | 30000 | 30000 | 25000 | 20000 |

It can be understood that rapid and sufficient sterilization can be achieved by performing both the vibrationally stirring and the ultraviolet-light irradiation, whereas the sterilizing effect is relatively low when the ultraviolet-light irradiation was conducted without performing the vibrationally stirring.

EXAMPLE 13

The test was conducted in the same manner as Example 1 except that the following: The vibration vane made of stainless steel coated with 15 $\mu$m thick silver layer was used. The vibration vane fixing member made of stainless steel coated with 15 $\mu$m thick silver layer was used. As the liquid to be treated, river water was used.

The result of the sterilization are shown in the following Table 14.

TABLE 14

| Treatment time (min.) | 0 | 10 | 30 | 60 | 90 |
|---|---|---|---|---|---|
| General bacteria (n/ml) | 1500 | 500 | 0 | 0 | 0 |
| Coliform bacteria (MPN/100 ml) | 9600 | 8000 | 5000 | 1600 | 200 |

It can be understood that sterilizing rate is relatively low as compared with Example 1, however, sufficient sterilization can be achieved When the test was conducted in the same manner as the above except that the treatment tank having an inner surface coated with 15 $\mu$m thick silver layer was used, the result was obtained as somewhat superior to those of Table 14 while inferior to those of Example 1 in which the vibration vane fixing member made of neodymium magnet was used.

EXAMPLE 14

The test was conducted in the same manner as Example 11 except that all the vibration vane fixing member made of stainless steel was used. When the vibrationally stirring was performed, the number of detected bacteria became zero with the treatment of 180 minutes. On the other hand, when the vibrationally stirring was not performed, there could not be found out the sterilizing effect. Therefore, it is preferable to use at least one vibration vane fixing member made of magnetic field generating material and to conduct the vibrationally stirring as Example 11.

EXAMPLE 15

The test was conducted in the same manner as Example 12 except that all the vibration vane fixing member made of stainless steel was used. When the vibrationally stirring was performed, the number of detected bacteria became zero with the treatment of 180 minutes. On the other hand, when the vibrationally stirring was not performed, the same result as Example 12 was obtained. Therefore, it is preferable to use at least one vibration vane fixing member made of magnetic field generating material and to conduct the vibrationally stirring as Example 12.

EXAMPLE 16

The test was conducted in the same manner as Example 4 except that the following: The vibration vane fixing member made of stainless steel coated with 15 μm thick silver layer on a pre-coated layer, which was the same material of the vibration vane, was used.

The result of the sterilization are shown in the following Table 15.

TABLE 15

| Treatment time (min.) | 0 | 10 | 30 | 60 | 120 | 180 |
|---|---|---|---|---|---|---|
| Number of Live Bacteria (CFU/ml) | $2.8 \times 10^3$ | $2 \times 10^3$ | $1.5 \times 10^3$ | $6.7 \times 10^2$ | $6.9 \times 10^2$ | $5.9 \times 10^2$ |

EXAMPLE 17

The test was conducted in the same manner as Example 1 except that the following: The vibration vane made of aluminum coated with 5 μm thick aluminum oxide layer obtained by anodizing process was used. As the liquid to be treated, pure water containing $4 \times 10^4$ n/ml of bacteria was used. After the treatment was conducted during 60 minutes, the number of bacteria was reduced to 200 n/ml.

When the treatment was conducted while the ultraviolet lamp (GL-13Q: manufactured by Matsushita Electric Industrial Co., Ltd., 13 W, 0.34 A, 25 mm in diameter, 344 mm in length; output of bactericidal line is 1.7 W) disposed in the liquid as shown in FIGS. 23 and 24 was turned on, the number of bacteria was reduced to 300 n/ml with the treatment of about 30 minutes.

EXAMPLE 18

The test was conducted in the same manner as Example 1 except the following: Various parts of food wrapping machine were used as the solid article to be treated. The parts were accommodated in a cage of wire mesh which was submerged in the liquid. The treatment was conducted at a room temperature during 20 minutes while the cage was rotated at a rotational frequency of 8 times per minute [Case 18-A].

For comparison, the test was conducted for a case where the treatment was performed in the same manner as Case 18-A except that the vibration vane and vibration vane fixing member both made of stainless steel were used [Case 18-B].

The result of the sterilization are shown in the following Table 16.

TABLE 16

| | General bacteria (n/ml) | | Yeast fungi (n/ml) | | Coliform bacteria | |
|---|---|---|---|---|---|---|
| Parts No. | 18-A | 18-B | 18-A | 18-B | 18-A | 18-B |
| 1 | 0 | 8 | 0 | 15 | – | – |
| 2 | 0 | 11 | 0 | 10 | – | – |
| 3 | 0 | 5 | 0 | 5 | – | + |
| 4 | 0 | 5 | 0 | 10 | – | + |
| 5 | 0 | 15 | 0 | 50 | – | + |
| 6 | 0 | 5 | 0 | 10 | – | – |
| 7 | 0 | 5 | 0 | 40 | – | + |
| 8 | 0 | 7 | 0 | 250 | – | + |
| 9 | 0 | | 0 | 50 | – | + |
| 10 | 0 | 80 | 0 | 300 | – | + |
| 11 | 0 | 20 | 0 | 20 | – | – |
| 12 | 0 | 10 | 0 | 5 | – | – |
| 13 | 0 | 30 | 0 | 5 | – | + |
| 14 | 0 | 150 | 0 | 150 | – | + |
| 15 | 0 | 200 | 0 | 200 | – | + |

+: detected
–: undetected

What is claimed is:

1. A vibrationally stirring apparatus for sterilizing liquid, or an article submerged in liquid or both by vibrationally stirring said liquid, said apparatus comprising:
   a vibration generating unit containing a vibration motor;
   at least one vibrating rod operationally connected to said vibration generating unit;
   at least one vibration vane fixed to said vibrating rod; and
   a vibration vane fixing member for fixing said vibration vane to said vibrating rod,
   wherein at least one of said vibration vane and said vibration vane fixing member has a surface of a material selected from the group consisting of silver, gold, an alloy of silver and gold, and a sterilizing metallic compound.

2. The vibrationally stirring apparatus as claimed in claim 1, wherein said sterilizing metallic compound is a metallic oxide.

3. The vibrationally stirring apparatus as claimed in claim 1, wherein said vibration generating unit is suitable for vibrating said vibration vane at an amplitude of 0.1 to 15.0 mm and at a vibrational frequency of 200 to 1000 times per minute in said liquid.

4. The vibrationally stirring apparatus as claimed in claim 1, further comprising an inverter for controlling said vibration motor so as to vibrate at a frequency of 10 to 200 Hz.

5. A sterilizing apparatus for liquid, or an article submerged in liquid or both, said apparatus comprising:
   a vibrationally stirring apparatus having a vibration generating unit containing a vibration motor, at least one vibrating rod operationally connected to said vibration generating unit, at least one vibration vane fixed to said vibrating rod, and a vibration vane fixing member for fixing said vibration vane to said vibrating rod; and
   a treatment tank for receiving said liquid, in which said vibration vane and said vibration vane fixing member are disposed,
   wherein at least one of said vibration vane and said vibration vane fixing member has a surface of a material selected from the group consisting of silver, gold, an alloy of silver and gold, and a sterilizing metallic compound.

6. The sterilizing apparatus as claimed in claim 5, further comprising a holder for holding said article in said treatment tank.

7. The sterilizing apparatus as claimed in claim 6, further comprising a driving means for moving said holder.

8. The sterilizing apparatus as claimed in claim 5, wherein said sterilizing metallic compound is a metallic oxide.

9. The sterilizing apparatus as claimed in claim 5, wherein said vibration generating unit is suitable for vibrating said vibration vane at an amplitude of 0.1 to 15.0 mm and at a vibrational frequency of 200 to 1000 times per minute in said liquid.

10. The sterilizing apparatus as claimed in claim 5, further comprising an inverter for controlling said vibration motor so as to vibrate at a frequency of 10 to 200 Hz.

11. A sterilizing method for liquid, or an article submerged in liquid or both, said method comprising:

providing a vibrationally stirring apparatus having a vibration generating unit containing a vibration motor, at least one vibrating rod operationally connected to said vibration generating unit, at least one vibration vane fixed to said vibrating rod, and a vibration vane fixing member for fixing said vibration vane to said vibrating rod, wherein at least one of said vibration vane and said vibration vane fixing member has a surface of a material selected from the group consisting of silver, gold, an alloy of silver and gold, and a sterilizing metallic compound;

submerging said vibration vane and said vibration vane fixing member in said liquid held in a treatment tank; and vibrating said vibration vane by said vibration generating unit to cause vibrational stirring of said liquid, thereby sterilizing said liquid.

12. The sterilizing method as claimed in claim 11, further comprising:

submerging said article in said liquid; and sterilizing said article by said vibrational stirring of said liquid.

13. The sterilizing method as claimed in claim 11, wherein said liquid is vibrationally stirred so as to have a flow rate of 100 mm/sec or more in each direction of three dimensions.

14. The sterilizing method as claimed in claim 11, wherein said sterilizing metallic compound is a metallic oxide.

15. The sterilizing method as claimed in claim 11, wherein said vibration generating unit is suitable for vibrating said vibration vane at an amplitude of 0.1 to 15.0 mm and at a vibrational frequency of 200 to 1000 times per minute in said liquid.

16. The sterilizing method as claimed in claim 11, wherein said vibration motor is vibrated at a frequency of 10 to 200 Hz.

17. The vibrationally stirring apparatus as claimed in claim 2, wherein said sterilizing metallic compound is titanium oxide film formed by surface oxidation treatment of titanium member or titanium alloy member.

18. The sterilizing apparatus as claimed in claim 8, wherein said sterilizing metallic compound is titanium oxide film formed by surface oxidation treatment of titanium member or titanium alloy member.

19. The sterilizing method as claimed in claim 14, wherein said sterilizing metallic compound is titanium oxide film formed by surface oxidation treatment of titanium member or titanium alloy member.

20. The sterilizing apparatus as claimed in claim 5, further comprising a device for irradiating at least one of said vibration vane and said vibration vane fixing member with ultraviolet-light, said device being disposed at the inside or outside of said treatment tank.

21. The sterilizing method as claimed in claim 11, further comprising irradiating at least one of said vibration vane and said vibration vane fixing member with ultraviolet-light while said liquid is vibrationally stirred.

22. The vibrationally stirring apparatus as claimed in claim 2 wherein said metallic oxide is selected from the group consisting of titanium oxide and zinc oxide.

23. The vibrationally stirring apparatus as claimed in claim 2 wherein said metallic oxide is in the form of particles dispersed in a matrix material.

24. The sterilizing apparatus as claimed in claim 8 wherein said metallic oxide is selected from the group consisting of titanium oxide and zinc oxide.

25. The sterilizing apparatus as claimed in claim 8 wherein said metallic oxide is in the form of particles dispersed in a matrix material.

26. The sterilizing method as claimed in claim 14 wherein said metallic oxide is selected from the group consisting of titanium oxide and zinc oxide.

27. The sterilizing method as claimed in claim 14 wherein said metallic oxide is in the form of particles dispersed in a matrix material.

28. A vibrationally stirring apparatus for sterilizing liquid, or an article submerged in liquid or both by vibrationally stirring said liquid, said apparatus comprising:

a vibration-generating unit containing a vibration motor;

at least one vibrating rod operationally connected to said vibration-generating unit;

at least one vibration vane fixed to vibrating rod; and a vibration-vane-fixing member for fixing said vibration vane to said vibrating rod, wherein at least one of said vibration vane and said vibration-vane-fixing member is made of magnetic-field-generating material.

29. The vibrationally stirring apparatus as claimed in claim 28 wherein said vibration-generating unit is suitable for vibrating said vibration vane at an amplitude of 0.1 to 15.0 mm and at a vibrational frequency of 200 to 1000 times per minute in said liquid.

30. The vibrationally stirring apparatus as claimed in claim 28 further comprising an inverter for controlling said vibration motor so as to vibrate at a frequency of 10 to 200 Hz.

31. A sterilizing apparatus for sterilizing liquid, or an article submerged in liquid or both, said apparatus comprising:

a vibrationally stirring apparatus having a vibration-generating unit containing a vibration motor, at least one vibrating rod operationally connected to said vibration-generating unit, at least one vibration vane fixed to said vibrating rod, and a vibration-vane-fixing member for fixing said vibration vane to said vibrating rod; and a treatment tank for receiving said liquid, in which said vibration vane and said vibration-vane-fixing member are disposed, wherein at least one of said vibration vane and said vibration-vane-fixing member is made of magnetic-field-generating material.

32. The sterilizing apparatus as claimed in claim 31 further comprising a holder for holding said article in said treatment tank.

33. The sterilizing apparatus as claimed in claim 32 further comprising a driving means for moving said holder.

34. The sterilizing apparatus as claimed in claim 31 wherein said vibration generating unit is suitable for vibrating said vibration vane at an amplitude of 0.1 to 15.0 mm and at a vibrational frequency of 200 to 1000 times per minute in said liquid.

35. The sterilizing apparatus as claimed in claim 31 further comprising an inverter for controlling said vibration motor so as to vibrate at a frequency of 10 to 200 Hz.

36. The sterilizing apparatus as claimed in claim 31 further comprising a device for irradiating at least one of said vibration vane and said vibration-vane-fixing member with ultraviolet light, said device being disposed at the inside or outside of said treatment tank.

37. A sterilizing method for liquid, or an article submerged in liquid or both, said method comprising:
   providing a vibrationally stirring apparatus having a vibration-generating unit containing a vibration motor, at least one vibrating rod operationally connected to said vibration-generating unit, at least one vibration vane fixed to said vibrating rod, and a vibration-vane-fixing member for fixing said vibration vane to said vibrating rod, wherein at least one of said vibration vane and said vibration-vane-fixing member is made of magnetic-field-generating material;
   submerging said vibration vane and said vibration-vane-fixing member in said liquid held in a treatment tank; and
   vibrating said vibration vane by said vibration-generating unit to cause vibrational stirring of said liquid, thereby sterilizing said liquid.

38. The sterilizing method as claimed in claim 37 further comprising:
   submerging said article in said liquid; and
   sterilizing said article by said vibrational stirring of said liquid.

39. The sterilizing method as claimed in claim 37 wherein said liquid is vibrationally stirred so as to have a flow rate of 100 mm/sec or more in each direction of three dimensions.

40. The sterilizing method as claimed in claim 37 wherein said vibration-generating unit is suitable for vibrating said vibration vane at an amplitude of 0.1 to 15.0 mm and at a vibrational frequency of 200 to 1000 times per minute in said liquid.

41. The sterilizing method as claimed in claim 37 wherein said vibration motor is vibrated at a frequency of 10 to 200 Hz.

42. The sterilizing apparatus as claimed in claim 37 further comprising irradiating at least one of said vibration vane and said vibration-vane-fixing member with ultraviolet light while said liquid is vibrationally stirred.

* * * * *